United States Patent [19]

Madabhushi et al.

[11] Patent Number: 5,567,292

[45] Date of Patent: Oct. 22, 1996

[54] POLYMERS FOR SEPARATION OF BIOMOLECULES BY CAPILLARY ELECTROPHORESIS

[75] Inventors: Ramakrishna S. Madabhushi, Foster City; Steven M. Menchen, Fremont; J. William Efcavitch, San Mateo; Paul D. Grossman, Burlingame, all of Calif.

[73] Assignee: The Perkin-Elmer Corporation, Foster City, Calif.

[21] Appl. No.: 350,852

[22] Filed: Dec. 6, 1994

Related U.S. Application Data

[63] Continuation-in-part of Ser. No. 170,078, Dec. 17, 1993, abandoned.

[51] Int. Cl.$^6$ ............................ C07K 1/26; C25B 7/00; C25B 15/00
[52] U.S. Cl. ................................. 204/451; 204/454
[58] Field of Search ........................ 204/180.1, 182.8, 204/299 R; 252/315.1

[56] References Cited

U.S. PATENT DOCUMENTS

| | | | |
|---|---|---|---|
| 4,963,243 | 2/1990 | Ogawa et al. | 204/229 R |
| 5,069,766 | 12/1991 | Zhu et al. | 204/180.1 |
| 5,164,055 | 11/1992 | Dubrow | 204/180.1 |
| 5,264,101 | 5/1992 | Demorest et al. | 240/299 R |

FOREIGN PATENT DOCUMENTS

WO92/22665  11/1993  WIPO.

OTHER PUBLICATIONS

Karger et al. Nucleic Acids Research 19(18):4955–4962 (1991) (no month) Multiwavelength fluorescence detection for DNA sequencing using capillary electrophoresis.

Smith et al. Methods in Enzymology vol. 155 pp. 260–301, Academic Press (1991). Methods in Enzymology 155:260–301, Academic Press (1991) (no month) The synthesis and use of fluorescent oligonucleotides in DNA sequence analysis.

Grant et al., Chemical Dictionary, 5th ed., p. 122.

*Primary Examiner*—John Niebling
*Assistant Examiner*—Edna Wong
*Attorney, Agent, or Firm*—Paul D. Grossman

[57] ABSTRACT

The invention provides uncharged water-soluble silica-adsorbing polymers for suppressing electroendoosmotic flow and to reduce analyte-wall interactions in capillary electrophoresis. In one aspect of the invention, one or more of such polymers are employed as components of a separation medium for the separation of biomolecules, such as polynucleotides, polysaccharides, proteins, and the like, by capillary electrophoresis. Generally, such polymers are characterized by (i) water solubility over the temperature range between about 20° C. to about 50° C., (ii) concentration in a separation medium in the range between about 0.001% to about 10% (weight/volume), (iii) molecular weight in the range of about $5 \times 10^3$ to about $1 \times 10^6$ daltons, and (iv) absence of charged groups in an aqueous medium having pH in the range of about 6 to about 9. In one embodiment, polymers of the invention are selected from the group consisting of polylactams, such as polyvinylpyrrolidone; N,N-disubstituted polyacrylamides; and N-substituted polyacrylamides. In accordance with the method of the invention, a sufficient amount of polymer adsorbs to the capillary surface to establish a zone of high viscosity that shields the analyte from the wall and impedes the movement of an electrical double layer under an electric field.

10 Claims, 27 Drawing Sheets

POLYMERS FOR SEPARATION OF BIOMOLECULES BY CAPILLARY ELECTROPHORESIS

RELATED U.S. APPLICATIONS

This is a continuation-in-part application of application Ser. No. 08/170,078 filed 17 Dec. 1993, now abandoned, which is hereby incorporated by reference.

FIELD OF THE INVENTION

The invention relates generally to the field of capillary electrophoresis, and more particularly to materials and methods for suppressing electroendoosmotic flow and analyte-wall interactions during separation of biomolecules, especially polynucleotides, by capillary electrophoresis.

BACKGROUND

Capillary electrophoresis has been applied widely as an analytical technique because of several technical advantages: (i) capillaries have high surface-to-volume ratios which permit more efficient heat dissipation which, in turn, permit high electric fields to be used for more rapid separations; (ii) the technique requires minimal sample volumes; (iii) superior resolution of most analytes is attainable; and (iv) the technique is amenable to automation, e.g. Camilleri, editor, Capillary Electrophoresis: Theory and Practice (CRC Press, Boca Raton, 1993); and Grossman et al, editors, Capillary Electrophoresis (Academic Press, San Diego, 1992). Because of these advantages, there has been great interest in applying capillary electrophoresis to the separation of biomolecules, particularly in nucleic acid analysis. The need for rapid and accurate separation of nucleic acids, particularly deoxyribonucleic acid (DNA) arises in the analysis of polymerase chain reaction (PCR) products and DNA sequencing fragment analysis, e.g. Williams, Methods 4:227–232 (19920; Drossman et at, Anal. Chem., 62: 900–903 (1990); Huang et at, Anal. Chem., 64:2149–2154 (1992); and Swerdlow et at, Nucleic Acids Research, 18:1415–1419 (1990).

Since the charge-to-frictional drag ratio is the same for different sized polynucleotides in free solution, electrophoretic separation requires the presence of a sieving medium. The initial sieving media of choice were gels, but problems of stability and manufacturability have led to the examination of non-gel liquid polymeric sieving media, such as linear polyacrylamide, hydroxyalkylcellulose, agarose, and cellulose acetate, and the like, e.g. Bode, Anal. Biochem., 83:204–210 (1977); Bode, Anal. Biochem., 83:364–371 (1977); Bode, Anal. Biochem., 92:99–110 (1979); Hjerten et at, J. Liquid Chromatography, 12:2471–2477 (1989); Grossman, U.S. Pat. No. 5,126,021; Zhu et al, U.S. Pat. No. 5,089111; Tietz et al, Electrophoresis, 13:614–616 (1992).

Another factor that complicates separations by capillary electrophoresis is the phenomena of electroendoosmosis. This phenomena, sometimes referred to as electroosmosis, is fluid flow in a capillary induced by an electrical field. It has impeded the application of capillary electrophoresis to situations where high resolution separations are required, such as in the analysis of DNA sequencing fragments. The phenomena arises in capillary electrophoresis when the inner wall of the capillary contains immobilized charges which cause the formation of a mobile layer of counter ions which, in turn, moves in the presence of an electrical field to create a bulk flow of liquid. Unfortunately, the magnitude of the electroendoosmotic flow can vary depending on a host of factors, including variation in the distribution of charges, selective adsorption of components of the analyte and/or separation medium, pH of the separation medium, and the like. Because this variability tends to reduce ones ability to resolve closely spaced bands analyte, many attempts have been made to directly or indirectly control such flow. The attempts have included covalent modification of the inner wall of the capillary to suppress charged groups, use of high viscosity polymers, adjustment of buffer pH and/or concentration, use of a gel separation medium covalently attached to the capillary wall, and the application of an electric field radial to the axis of the capillary, e.g. Hayes et at, Anal. Chem., 65:2010–2013 (1993); Drossman et al (cited above); Hjerten, U.S. Pat. No. 4,680,201; Van Alstine et al, U.S. Pat. No. 4,690,749; Wiktorowicz et al, Electrophoresis, 11:769–773 (1990); Belder et at, J. High Resolution Chromatography, 15:686–693 (1992).

Most of these approaches have met with mixed success or have only been used in the separation of analytes quite different chemically from nucleic acids. In particular, the use of capillary gels for DNA separations have been hampered by manufacturing problems and problems of stability and reliability during use, e.g. Swerdlow et al, Electrophoresis, 13:475–483 (1992).

In view of the strong scientific and industrial interest in being able to conveniently and accurately separate a variety of biomolecules, particularly polynucleotides, it would be desirable to have available a low viscosity electrophoretic separation medium capable of suppressing electroendoosmotic flow and of reducing analyte-wall interactions.

SUMMARY OF THE INVENTION

The invention relates to the use of uncharged water-soluble silica-adsorbing polymers to suppress electroendoosmotic flow and to reduce analyte-wall interactions in capillary electrophoresis. In one aspect of the invention, one or more of such polymers are employed as components of a separation medium for the separation of biomolecules, preferably polynucleotides, by capillary electrophoresis. Generally, such polymers are characterized by (i) water solubility over the temperature range between about 20° C. to about 50° C., (ii) concentration in a separation medium in the range between about 0.001% to about 10% (weight/volume), (iii) molecular weight in the range of about $5 \times 10^3$ to about $1 \times 10^6$ daltons, and (iv) absence of charged groups in an aqueous medium having pH in the range of about 6 to about 9. Preferably, such polymers of the invention are substantially non-hydroxylic. In one embodiment, polymers of the invention are selected from the group consisting of polyvinylactams, such as polyvinylpyrrolidone; N,N-disubstituted polyacrylamides; and N-substituted polyacrylamides. More preferably, such polymers of the invention are poly(N,N-dimethylacrylamide).

In accordance with the method of the invention, a sufficient amount of polymer adsorbs to the silica surface to establish a zone of high viscosity at the silica surface that impedes the movement of an electrical double layer under an electric field and that shields the analyte from the wall.

The invention includes methods of using the polymers of the invention to separate biomolecules, especially polynucleotides, by capillary electrophoresis; compositions comprising polymers of the invention for electrophoretically separating biomolecules in capillaries; and methods of using the separation medium of the invention for sequencing DNA.

The invention enhances the precision of biomolecule separation by electrophoresis in a capillary by dynamically suppressing electroendoosmotic flow and wall-analyte interactions through the adsorption of the uncharged polymers of the invention onto the surface of the capillary. Suppression is dynamic in the sense that throughout the separation process polymers of the invention adsorb and desorb from the surface of a capillary in equilibrium with polymer in solution in the separation medium. Thus, a constant degree of suppression is maintained not only during a separation run, but also from separation run to separation run.

DEFINITIONS

Figure 1:
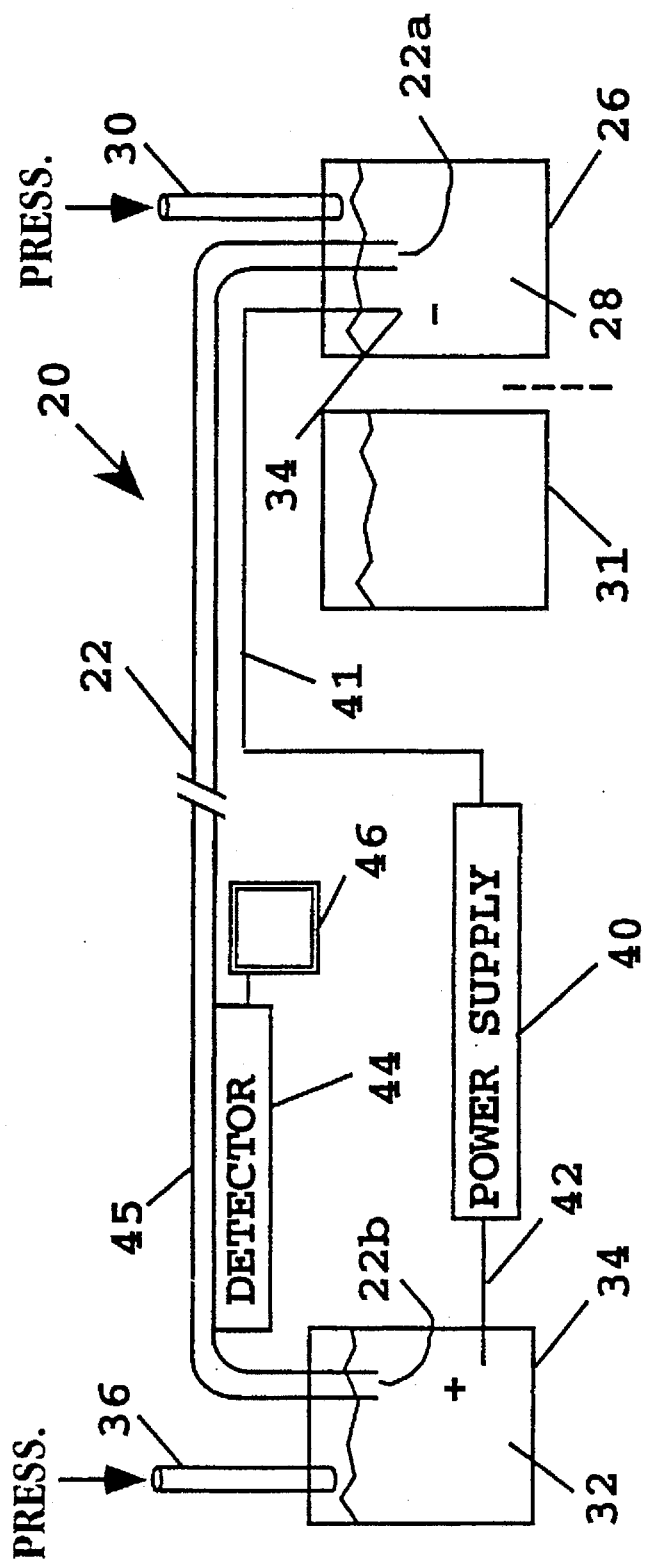
FIG. 1 diagrammatically illustrates an apparatus for carrying out capillary electrophoresis.

The term "capillary" as used herein refers to a tube or channel or other structure capable of supporting a volume of separation medium for carrying out electrophoresis. The geometry of a capillary may vary widely and includes tubes with circular, rectangular or square cross-sections, channels, groves, plates, and the like, and may be fabricated by a wide range of technologies. An important feature of a capillary for use with the invention is the surface-to-volume ratio of the surface in contact with the volume of separation medium. High values of this ratio permit better heat transfer from the separation medium during electrophoresis. Preferably, values in the range of about 0.4 to 0.04 are employed. These correspond to the surface-to-volume ratios of tubular capillaries with circular cross-sections having inside diameters in the range of about 10 μm to about 100 μm. Preferably, capillaries for use with the invention are made of silica, fused silica, quartz, silicate-based glass, such as borosilicate glass, phosphate glass, alumina-containing glass, and the like, or other silica-like materials.

The term "biomolecule" means a molecule typically synthesized by a biological organism that is water soluble and charged in the pH range of from about 6 to about 9. Preferably, the term biomolecule includes proteins, glycoproteins, natural and synthetic peptides, alkaloids, polysaccharides, polynucleotides, and the like. More preferably, the term biomolecule refers to polynucleotides.

The term "polynucleotide" as used herein refers to linear polymers of natural or modified nucleoside monomers, including double and single stranded deoxyribonucleosides, ribonucleosides, α-anomeric forms thereof, and the like. Usually the nucleoside monomers are linked by phosphodiester bonds or analogs thereof to form polynucleotides ranging in size from a few monomeric units, e.g. 8–40, to several thousands of monomeric units. Whenever a polynucleotide is represented by a sequence of letters, such as "ATGCCTG," it will be understood that the nucleotides are in 5'–>3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoroselenoate, phosphorodiselenoate, phosphoroanilothioate, phosphoranilidate, phosphoramidate, and the like.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described generally by Scheit, Nucleotide Analogs (John Wiley, New York, 1980).

The term "electroendoosmosis" or "electroendoosmostic flow" as used herein refers to the bulk flow of liquid due to the influence of an electric field on the layer of mobile counter ions adjacent to fixed, or immobile, charges on a surface, such as a capillary wall. Electroendoosmotic flow is typically measured as the mobility ($cm^2$/sec-volts) of a test analyte through a capillary tube under a standard set of conditions, e.g. determining buffer concentration and type, tube length, electrical field strength, and the like.

The term "polymer" is a large molecule composed of smaller monomeric subunits covalently linked together in a characteristic fashion. A "homopolymer" is a polymer made up of only one kind of monomeric subunit. A "copolymer" refers to a polymer made up of two or more kinds of monomeric subunits. As used herein the term "polymer" includes homopolymers and copolymers. A "monodisperse" polymer solution means that the polymer molecules in solution have substantially identical molecular weights. A "polydisperse" polymer solution means that the polymer molecules in solution have a distribution of molecular weights.

The term "non-hydroxylic" as used herein in reference to polymers means that the monomers used in the synthesis of a polymer contain no hydroxyl substituents.

DETAILED DESCRIPTION OF THE INVENTION

The invention provides a convenient means for suppressing electroendoosmotic flow and wall-analyte interactions during the separation of biomolecules, particularly DNA, by capillary electrophoresis. As used herein, the term "separation medium" refers to the medium in a capillary in which the separation of analyte components takes place. Separation media typically comprise several components, at least one of which is a charge-carrying component, or electrolyte. The charge-carrying component is usually part of a buffer system for maintaining the separation medium at a constant pH. Media for separating polynucleotides, or other biomolecules having different sizes but identical charge-frictional drag ratios in free solution, further include a sieving component. In addition to such conventional components, the separation medium of the invention comprise a surface interaction component. In the case of polynucleotide separations, the sieving component may be the same or different than the surface interaction component, but is usually different. The surface interaction component comprises one or more uncharged water-soluble silica-adsorbing polymers having the physical properties set forth above. Preferably, such one or more uncharged water-soluble silica-adsorbing polymers are non-hydroxylic. In further preference for polynucleotide separations, the sieving component of the separation medium of the invention comprises one or more uncrosslinked, particularly linear, polymers. Preferably, the components of the separation medium of the invention are selected so that its viscosity is low enough to permit rapid re-filling of capillaries between separation runs. For typical capillaries, e.g. 20–100 µm inside diameter and 40–60 cm in length, in the absence of a sieving component, viscosity is preferably less than 1000 centipoise, and more preferably, between about 1 to about 300 centipoise. In the presence of a sieving component, viscosity is preferably less than 5000 centipoise, and more preferably, less than 1000 centipoise.

Polymers for use as the surface interaction component of the separation medium may belong to a variety of chemical classes, such as those described in the following references: Molyneux, Water-Soluble Synthetic Polymers: Properties and Behavior, Volumes I and II (CRC Press, Boca Raton, 1982); Davidson, Editor, Handbook of Water-Soluble Gums and Resins (McGraw-Hill, New York, 1980); Franks, editor, Water: A Comprehensive Treatise (Plenum Press, New York, 1973); and the like. Preferably, the uncharged water-soluble silica-adsorbing polymers of the invention include, but not limited to, N,N-disubstituted polyacrylamides, N-monosubstituted polyacrylamides, polymethacrylamide, polyvinylpyrrolidone, and the like. Exemplary substituents of the polyacrylamides include $C_1$ to $C_{12}$ alkyl; halo-substituted $C_1$ to $C_{12}$ alkyl; methoxy-substituted $C_1$ to $C_{12}$ alkyl; hydroxyl-substituted $C_1$ to $C_{12}$ alkyl and the like. Preferably, the halo substituent is fluoro and the hydroxyl-substituted $C_1$ to $C_{12}$ alkyl is monosubstituted. It is understood that the above monomer substituents are selected so that the resulting polymer is water soluble. For example, it is clear that $C_{12}$ alkyl-containing monomer could only be present as a small fractional component of a copolymer. More preferably, exemplary substituents are selected from the group consisting of $C_1$ to $C_3$ alkyl; halo-substituted $C_1$ to $C_3$ alkyl; methoxy-substituted $C_1$ to $C_3$ alkyl; and hydroxyl-substituted $C_1$ to $C_3$ alkyl.

Such polymers are synthesized by conventional techniques, e.g. as disclosed in Odian, Principles of Polymerization, Third Edition (John Wiley, New York, 1991). An important feature of the invention is that the polymer of the surface interaction component be uncharged. Preferably, polymers of the invention are synthesized under non-aqueous conditions so that uncharged initiators can be used. Such conditions also preclude the incorporation of charged initiators into the product. The polymers comprising the surface interaction component of the separation medium may be present at a concentration of from about 0.001% to about 10% (w:v). Preferably, such polymers are present at a concentration in the range of about 0.01% to about 6%.

The silica-adsorbing quality of the preferred polymers can be measured in a number of well-known ways, such as by ellipsometry, determining changes in the hydrodynamic properties of adsorbent test particles, determination of adsorption isotherms, or like methods. Such techniques are described in Malmsten et al, Macromolecules, 25:2474–2481 (1992); Rob and Smith, European Polymer J., 10: 1005–1010 (1974); Vincent et al Surf. Colloid Sci., 12:1–117 (1982); Takahashi et al, Advances in Polymers Science, 46: 1–65. (1982), and like references. An adsorption isotherm is a graphical presentation of the adsorption exerted by an adsorbent on a solution of a given substance at a fixed temperature. The determination of adsorption isotherms require the preparation of solutions of known concentrations of the material whose adsorption is to be measured (the adsorbate). The adsorbate solutions are combined with known quantities of the material (the adsorbent) whose surface the adsorbate adheres to. Once an equilibrium is reached between the adsorbate in solution and the adsorbate on the surface of the adsorbent, the concentration of the adsorbate solution is determined. The reduction in concentration of the solution is a measure of the degree of adsorption of the adsorbate under the standard conditions.

The degree of adsorption may also be measured indirectly by observing the reduction of electroendoosmotic flow under a set of standard values of the following parameters: buffer type and concentration, temperature, electric field strength, capillary type, diameter, and length, and test analyte. An exemplary standard for such measurement is as follows: Uncoated fused silica capillary 40 cm in total length, 20 cm to detector (UV), 75 µm inside diameter; 0.1M glycylglycine buffer (pH 8.0); marker solution of 0.92 mM mesityl oxide and 1 mM p-toluenesulfonic acid (p-TSA); electrophoresis at 30° C. under 10 kV. The polymer being tested is added to the buffer. With no surface interaction component, the electroendoosmotic flow is approximately $6\times10^{-4}$ $cm^2$/sec-volts. Preferably, in such a separation medium, a sufficient concentration of polymer of the invention is employed to reduce electroendoosmotic flow to less than about $2\times10^{-5}$ $cm^2$/sec-volts.

For polynucleotide separations, the silica-adsorbing quality of a polymer of the invention is preferably characterized by the relationship between resolving power and polynucleotide length for a selected "ladder" of polynucleotides under a standard set of conditions. Resolving power is conveniently expressed in terms of the number of theoretical plates, N, of the test system. $N=(L/\sigma)^2$ where L is the average path length of a test analyte under a peak from injection port to detector (usually position of peak maximum) and $\sigma$ is the variance of the peak. Preferably, polymers of the invention provide a substantially linear relationship between number of theoretical plates and size of polynucleotide over the range of from about 100 to about 500 nucleotides; more preferably, the relationship is linear over the range of from about 20 to about 600 nucleotides. A standard set of conditions for generating theoretical plates versus polynucleotide length curves is described below.

Exemplary ladders of different-sized polynucleotides in the above-mentioned size ranges are available in commercially available kits, e.g. the 100 basepair double stranded DNA ladder from BRL-GIBCO, the Taq DNA Sequencing Standard from Applied Biosystems, Inc., or the like. A standard separation medium can be prepared as follows:

0.60g of acrylamide (ultrapure, ICN, Costa Mesa, Calif.) is dissolved in 10 ml 1× TBE, 30% formamide, 3.5M urea buffer, filtered (0.2 μm pore size), and degassed. The monomer solutions are polymerized by addition at room temperature of 1 μl of 100% N,N,N',N'-tetramethylethylenediamine (TEMED) and 2 μl ammonium persulfate, 10% w:v in water (APS), per ml of monomer solution (to give a final concentration of 0.02% w:v APS and 0.1% v:v TEMED).

The above separation medium is loaded into a 55 cm uncoated fused silica capillary tube, 50 μm inside diameter, 40 cm to detector. The capillary may be used in a commercially available capillary electrophoresis apparatus having fluorescence detection capability. Fluorescence detection systems for detecting fluorescently labelled analytes in capillaries is well known in the art, e.g. Mathies et at, U.S. Pat. No. 5,091,652; Mathies et al, International Application No. PCT/US93/01607; Ruiz-Martinez et at, Anal. Chem. 65: 2851–2858 (1993); and the like. The DNA fragments from the standard are denatured and loaded electrokinetically as follows: The dried sample is resuspended in a mixture of 5 mM aqueous EDTA (0.5 μl) and formamide (6 μl). The suspension is heated at 90° C. for 2 minutes then transferred to an ice bath. The ladder is loaded by placing the cathode and cathodic end of the capillary into the above solution then applying 6 kV across the tube for 5 seconds. Separation of the DNA fragments in the ladder commences by returning the cathode and cathodic end of the capillary into the cathode reservoir and applying a running voltage of 12 kV.

Apparatus for carrying out capillary electrophoresis is well-known and is not a critical feature of the invention. Many references are available describing the basic apparatus and several capillary electrophoresis instruments are commercially available, e.g. Applied Biosystems (Foster City, Calif.) model 270A instrument. Exemplary references describing capillary electrophoresis apparatus and their operation include Jorgenson, Methods, 4:179–190 (1992); Colburn et at, Applied Biosystems Research News, issue 1 (winter 1990); Grossman et al (cited above); and the like. FIG. 1 is a schematic representation of an exemplary capillary electrophoresis system 20 suitable for practicing the invention. However, as mentioned above, a wide variety of systems are amenable for use with the invention in addition to that represented in the figure, e.g. as described in Harrison et al, Science, 261:895:897 (1993); Pace, U.S. Pat. No. 4,908,112; Kambara et al, U.S. Pat. No. 5,192,412; Seiler et at, Anal. Chem., 65:1481–1488 (1993); and the like. In the figure, capillary tube 22 preferably has a length between about 10 to 200 cm, typically less than about 100 cm, and a preferred inner diameter in the range of about 10 to 200 μm, and more typically in the range of about 50 to 75 μm, e.g. available from Polymicro Technologies (Phoeniz, Ariz.). Preferably, there is no coating on the inside surface of the tube. A cathodic reservoir 26 in system 20 contains a separation medium 28, described further below. The cathodic end 22a of capillary tube 22 is sealed within reservoir 26 and is immersed in the separation medium during electrophoresis. Second tube 30 in reservoir 26 is connected to a finely controlled air pressure system which can be used to control the pressure in the head space above the separation medium, e.g. for loading separation medium into the capillary tube by positive pressure. Sample reservoir 31 contains the sample mixture to be loaded into the cathodic end of capillary 22. The anodic end 22b of capillary 22 is immersed in separation medium 32 contained in anodic reservoir 34. A second tube 36 in reservoir 34 can be included to control the pressure above separation medium 32. High voltage supply 40 is connected to the cathodic and anodic reservoirs by electrodes 41 and 42. High voltage supply 40 produces a constant potential across the electrodes in the range of a few kilovolts (kV) to 60 kV, with a potential in the range of about 10 to 30 kV being typical. Currents through the capillary are generally in the microamp range, typically between a few to 100 μA, with 20 μA being typical. Detector 44 positioned adjacent to capillary 22 monitors sample peaks migrating through optical detection zone 45 of the capillary. Typically, optical detection zone 45 comprises a region of capillary 22 in which the ususal polyimide coating has been removed to permit UV and/or visible light, e.g. fluorescence, detection of the separated analyte. A wide variety of detection schemes are amenable for use with the invention, including UV absorption, fluorescence emission, conductance, radioactive emission, and the like. For example, detection systems for fluorescent analytes are described in Zare et al, U.S. Pat. No. 4,675,300 and Folestad et al, U.S. Pat. No. 4,548,498.

As mentioned above, separation medium of the invention generally comprises three components: a charge-carrying component, a sieving component, and a surface interaction component. Additional components may also be included in particular embodiments, such as denaturants when it is desirable to prevent the formation of duplexes or secondary structures in polynucleotides. Preferred denaturants include formamide, e.g. 40–90%, urea, e.g. 6–8M, commercially available lactams, such as pyrrolidone, and the like. Guidance for their use in electrophoresis can be found in well known molecular biology references, e.g. Sambrook et al, Molecular Cloning: A Laboratory Manual, Second Edition (Cold Spring Harbor Laboratory, New York, 1989).

Typically, a buffer system for controlling pH is employed as the charge-carrying component. Exemplary buffers include aqueous solutions of organic acids, such as citric, acetic, or formic acid; zwitterionics, such as TES (N-tris[hydroxymethyl]-2-aminoethanesulfonic acid, BICINE (N,N-bis[2-hydroxyethyl]glycine, ACES (2-[2-amino-2-oxoethyl)-amino]ethanesulfonic acid), or glycylglycine; inorganic acids, such as phosphoric; and organic bases, such as Tris (Tris[hydroxymethyl]aminomethane) buffers, e.g. available from Sigma. Buffer concentration can vary widely, for example between about 1 mM to 1M, but are typically about 20 mM. Exemplary buffer solutions for conventional capillary electrophoresis applications include the following: (i) 0.1M Tris, 0.25M boric acid, 7M urea with a pH of 7.6 for single stranded polynucleotide separations; or (ii) 0.089M Tris, 0.089M bode acid, 0.005M EDTA for double stranded polynucleotide separations. For non-zwitterionic buffer systems, preferably PDMA or polyvinylpyrrolidone are employed as the surface interaction component.

Sieving components of electrophoretic separation media are well known in the art and are disclosed in Zhu et al, U.S. Pat. No. 5,089,111; Ruiz-Martinez et al, Anal. Chem., 65:2851–2858 (1993); Williams, Methods, 4:227–232 (1992); and like references. Preferably, the sieving component of the separation medium of the invention is a low-viscosity entangled polymer solution as taught by Grossman, U.S. Pat. No. 5,126,021. A low viscosity separation medium is preferred so that capillaries can be readily re-filled in automated systems, e.g. for large-scale DNA sequencing applications. The rate of solution flow through the capillary determines how much time is required to replace the separation medium between successive analyses. Guidance for synthesizing entangled polymers with a range of viscosities suitable for DNA sieving applications is provided by Grossman, which is incorporated by reference. Generally, the viscosity of a polymer, or copolymer, solution is determined by the molecular weight (MW) and concentration of the polymer or copolymer components of the separation medium. The molecular weight of a polymer or copolymer can be adjusted during synthesis in a number of ways well known in the art, e.g. as reviewed in Odian, Principles of Polymerization, Third Edition (John Wiley, New York, 1991), or like references.

A second approach for controlling the average MW of a polymer or copolymer used in the invention is by fractionating a polydisperse polymer product into different MW fractions followed by purification. Typical fractionation techniques include gel permeation chromatography, dialysis using membranes having specific MW cutoffs, fractional precipitations in water-miscible solvents, such as methanol, and the like.

For apparatus employing conventional capillary tubes, it is clear that the upper limits of polymer or copolymer MW and/or concentration is dictated primarily by the upper viscosity that can be pushed or pulled through the tubes. For example, if short capillaries (length of about 20 cm) with large inside diameters (IDs) (e.g. radius of about 0.01 cm) are employed, a solution with a viscosity of as much as 38,000 centipoise could be pushed through the capillary in 30 minutes at high pressure, e.g. 100 psi. For more conventional capillary tubes, e.g. 50 μm ID and 50 cm in length, a viscosity in the range of about 10–1000 centipoise permits separation medium to be replaced within about 30 minutes using a pressure differential across the tube of between about 50–100 psi.

Exemplary sieving polymers include linear polyoxides; polyethers, such as polyethylene oxide and polypropylene oxide; polyacrylamide; polymethacrylamide; polyvinylpyrrolidone; polyvinyloxazolidone; and a variety of water-soluble hydroxylic polymers, such as water-soluble natural gums, such as dextran; water-soluble cellulose compounds, such as methylcellulose and hydroxyethylcellulose, and copolymers and blends of these polymers. Preferably, such polymers are used at a concentration in the range between about 0.5% and 10% w:v.

Double stranded polynueleotides, e.g. DNA fragments from PCR or LCR amplifications, enzyme digests, or the like, are separated by standard protocols, or manufacturer's suggested protocols where a commercial capillary electrophoresis instrument is employed, e.g. a model 270-HT instrument (Applied Biosystems, Inc., Foster City). The only exception to such standard or suggested protocols is that the separation medium of the invention is employed.

DNA sequencing in accordance with the invention requires the separation of single stranded polynueleotides prepared by DNA sequencing protocols, e.g. described in Sambrook et at, Molecular Cloning: A Laboratory Manual, Second Edition (Cold Spring Harbor Laboratory, New York, 1989); Ausubel et al, Current Protocols in Molecular Biology (John Wiley & Sons, Media, Pa.); or the like.

The important feature of currently available DNA sequencing protocols is the generation of a "nested series" or "ladder" of single stranded polynucleotides, or DNA sequencing fragment, that must be separated by size. The basic steps of the chain-termination approach to DNA sequencing are (1) providing an oligonueleotide primer and a template nucleic acid containing, as a subsequence, a target nucleic acid whose sequence is to be determined, (2) hybridizing the oligonucleotide primer to the template nucleic acid, (3) extending the primer with a nucleic acid polymerase, e.g. T7 DNA polymerase, Sequenase™, a reverse transcriptase, or the like, in a reaction mixture containing nucleoside triphosphate precursors and at least one chain terminating nucleotide to form a nested series of DNA fragment populations, such that every shorter DNA fragment is a subsequence of every longer DNA fragment and such that each DNA fragment of the same size terminates with the same chain-terminating nucleotide, (4) separating the DNA fragment populations according to size, and (5) identifying the chain-terminating nucleotide associated with each DNA fragment population.

As used herein, the term "nucleoside triphosphate precursors" refers to deoxyadenosine triphosphate (ATP), deoxycytidine triphosphate (CTP), deoxyguanosine triphosphate (GTP), and thymidine triphosphate (TTP), or analogs thereof, such as deoxyinosine triphosphate (ITP), 7-deazadeoxyguanosine triphosphate, and the like.

A template is provided in accordance with the teachings in the art, e.g. Technical Manual for Model 370A DNA Sequencer (Applied Biosystems, Inc., Foster City, Calif.). For example, the target sequence may be inserted into a suitable cloning vector, such as the replicatire form of an M13 cloning vector, which is then propagated to amplify the number of copies of the target sequence. The single-stranded form of M13 is isolated for use as a template. Alternatively, a template can be provided by polymerase chain reaction (PCR) as taught in the art, e.g. Innis et al, (cited above); Wilson et al, Biotechniques, Vol. 8, pgs. 184–189 (1990); Gyllensten, Biotechniques, Vol. 7, pgs. 700–708 (1989); and the like. After amplification, the template can be used in the polymerization reaction(s) either in liquid phase or attached to a solid phase support, e.g. as taught by Stahl et al, Nucleic Acids Research, Vol. 16, pgs. 3025–3038 (1988); Hultman et al, Nucleic Acids Research, Vol. 17, pgs. 4937–4946 (1989); or the like.

Once the nested series DNA fragments are generated, they are separated by capillary electrophoresis using the separation medium of the invention.

EXAMPLE 1

Synthesis of PDMA in dioxane using AIBN

Poly(N,N-dimethylacrylamide) (pDMA) is synthesized using conventional techniques, e.g. as disclosed in T rossarelli et al, J. Polymer Sci., 57:445–452 (1962). Known amounts of dimethylacrylamide (DMA), dioxane, and azobisisobutyronitrile (AIBN) were mixed in an Eriemeyer flask and argon gas was bubbled through the solution for 10 minutes at room temperature. Polymerization was initiated by raising the temperature to 55° C. Polymerization times ranged from 10 to 25 minutes depending on the concentration of monomer. After polymerization, the resulting polymer was purified by three cycles of precipitation in hexane and dissolution in $CH_2Cl_2$. Finally, the hexane precipitate was dried overnight in a vacuum desiccator then lyophilized. The table below summarizes the reaction conditions for the various experiments.

| Batch No. | Monomer Concentration (% w/v) | Dioxane(cc) | AIBN (mg) | Estimated Average Molecular Weight* |
|---|---|---|---|---|
| RM1 | 70 | 14.3 | 12 | 79 kd |
| RM2 | 60 | 17.0 | 14 | 92 kd |
| RM3 | 50 | 20.0 | 16 | 99 kd |
| RM4 | 40 | 25.0 | 21 | 97 kd |
| RM5 | 30 | 33.3 | 27 | 83 kd |

-continued

| Batch No. | Monomer Concentration (% w/v) | Dioxane(cc) | AIBN (mg) | Estimated Average Molecular Weight* |
|---|---|---|---|---|
| RM6 | 20 | 50.0 | 41 | — |
| RM7 | 10 | 100.0 | 82 | 69 kd |
| RM8 | 5 | 200.0 | 164 | 54 kd |

*Estimated by gel permeation chromatography (peak mol. wt.).

EXAMPLE 2

Synthesis of PDMA in t-butyl alcohol using AIBN

Further polymerizations were carded out with t-butyl alcohol (t-BuOH) using the following protocol: Known amounts ofDMA monomer, t-butyl alcohol, and AIBN were combined, and argon gas was bubbled through the solutions for 20 minutes. The mixtures were brought to 55° C. and allowed to polymerize for 15 minutes. The resulting polymers were isolated as described in Example 1. The table below summarizes the reaction conditions for the various experiments.

| Batch No. | Monomer Concentration (% w/v) | t-BuOH (cc) | AIBN (mg) | Monomer (g) | Estimated Average Molecular Weight |
|---|---|---|---|---|---|
| RM17 | 50 | 20.0 | 16 | 10 | 81 kd |
| RM18 | 50 | 60.0 | 50 | 30 | 107 kd |
| RM19 | 70 | 14.0 | 12 | 10 | 99 kd |
| RM21 | 70 | 72.0 | 60 | 50 | 112 kd |

*Estimated by gel permeation chromatography (peak mol. wt.).

EXAMPLE 3

Change in Electroendoosmotic Flow in Test System by Various Poly(dimethylacrylamide) Solutions The effect of various formulations of PDMA on electroendoosmotic flow in a test system was measured. The test system consisted of an Applied Biosystems model 270 HT capillary electrophoresis instrument configured in the following manner: Uncoated fused silica capillary 40 cm in total length, 20 cm to detector (UV), 75 µm inside diameter was installed; the separation medium consisted of a 0.1M glycylglycine buffer (pH 8.0) with the test PDMA polymer added; a marker solution consisted of 0.92 mM mesityl oxide; and electrophoresis took place at 30° C. under 10 kV after electrokinetic loading as described above. The results are listed in the table below:

| PDMA | Concentration | Electroendoosmotic Flow* |
|---|---|---|
| RM8 | 0.1% (w:v) | $7.38 \times 10^{-5}$ |
| RM16 | 0.1% (w:v) | $2.73 \times 10^{-5}$ |
| RM18** | 0.01% (w:v) | $1.98 \times 10^{-5}$ |

*cm²/sec-volts
**p-TSA (1 mM in H$_2$O) used as marker.

EXAMPLE 4

Figure 2:
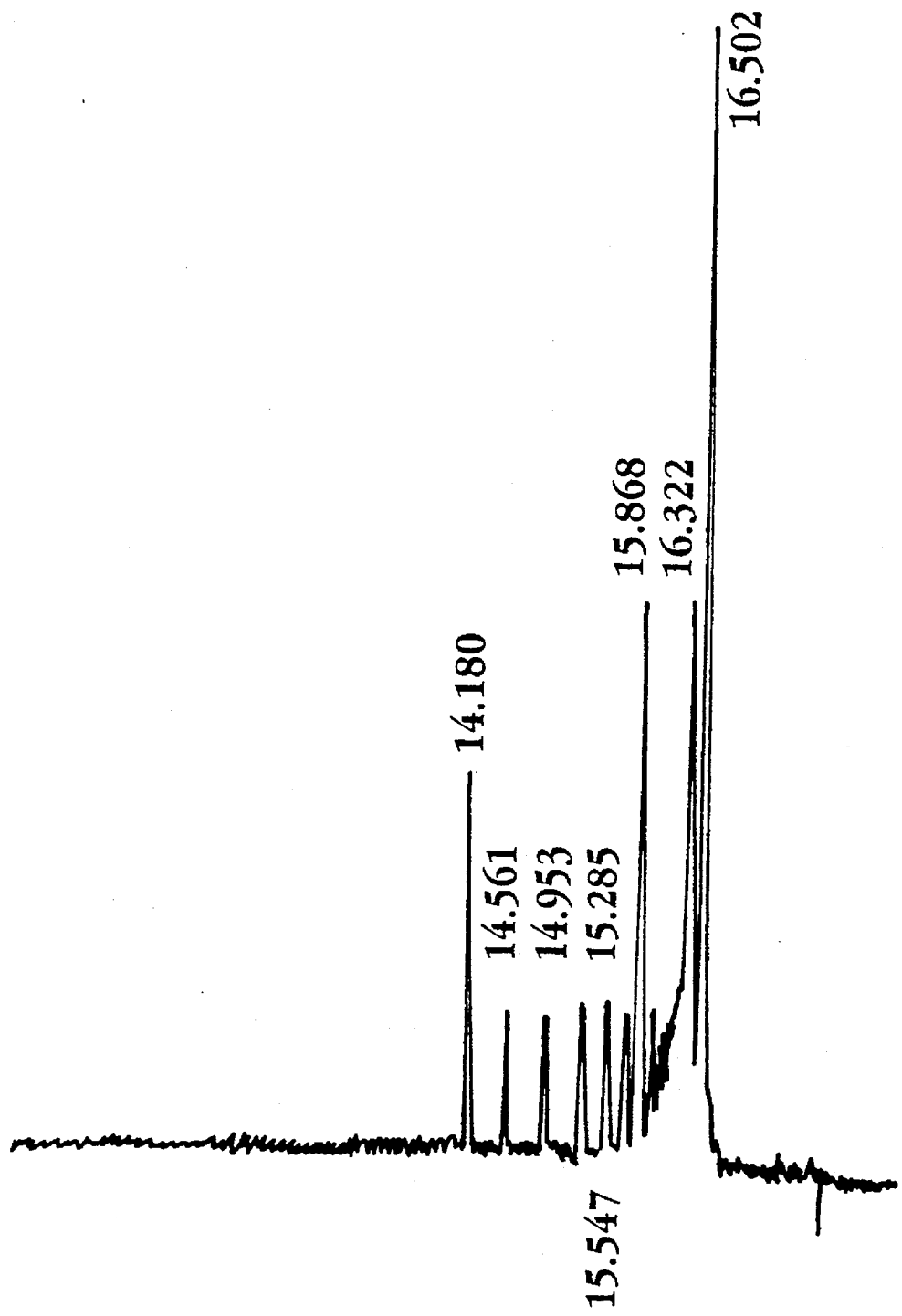
FIG. 2 is an electropherogram of a 100 basepair DNA ladder separated in a 3% poly(dimethyacrylamide) solution (RM8) in a glycylglycine buffer.

Electrophoresis of 100 basepair DNA ladder using 3% RM8 in a 0.1M Glycylglycine Buffer A 3% (w:v) RM8 PDMA polymer in a 0.1M glycylglycine buffer was used to separate the components of a commercial double stranded DNA ladder (100 bp DNA ladder, GIBCO-BRL). An Applied Biosystems model 270 HT was fitted with a 75 µm inside diameter uncoated fused silica capillary having 60 cm total length and 40 cm from the sample injection port to detector. Electrophoresis was carried out under 10 kV and 13 µA at 30° C. The sample was electrokinetically injected under 5 kV and 6 µA for 5 seconds. An electropherogram of the analyte (showing UV absorption at 260 nm) is illustrated in FIG. 2.

EXAMPLE 5

Figure 3:
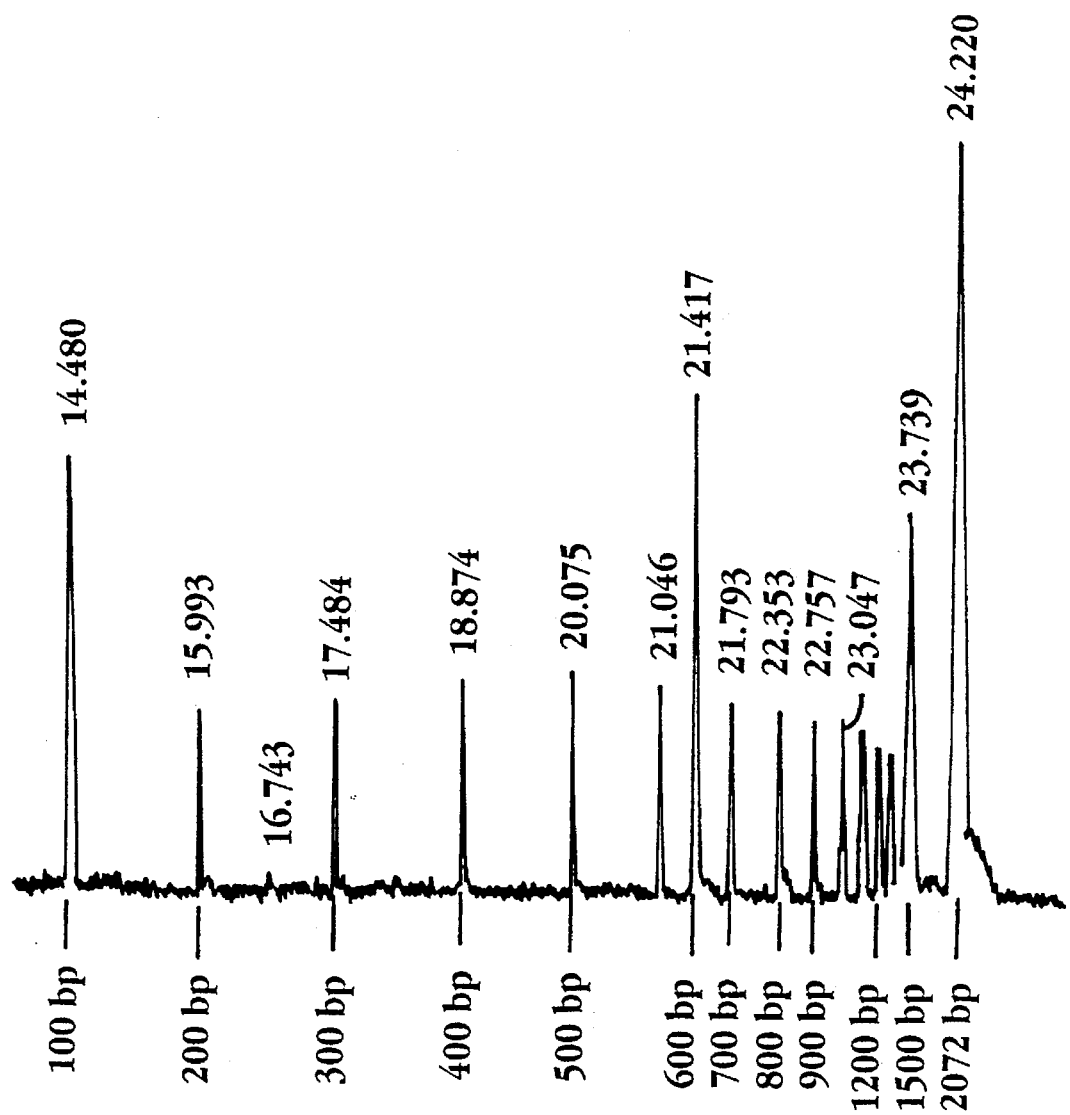
FIG. 3 is an electropherogram of a 100 basepair DNA ladder separated in a 3% poly(dimethyacrylamide) solution (RM18) in a glycylglycine buffer.

Electrophoresis of 100 basepair DNA ladder using 3% RM18 in a 0.1M Glycylglycine Buffer A 3% (w:v) RM18 PDMA polymer in a 0.1M glycylglycine buffer pH 8.0 was used to separate the components of the double stranded DNA ladder of Example 4. An Applied Biosystems model 270 HT was fitted with a 75 µm inside diameter uncoated fused silica capillary having 60 cm total length and 40 cm from the sample injection port to detector. Electrophoresis was carried out under 10 kV and 13 µA at 30° C. The sample was electrokinetically injected under 5 kV and 7 µA for 5 seconds. An electropherogram of the analyte (showing UV absorption at 260 nm) is illustrated in FIG. 3.

EXAMPLE 6

Electrophoresis of 100 basepair DNA ladder using 3% RM18 in a 90 mM TBE Buffer

Figure 4:
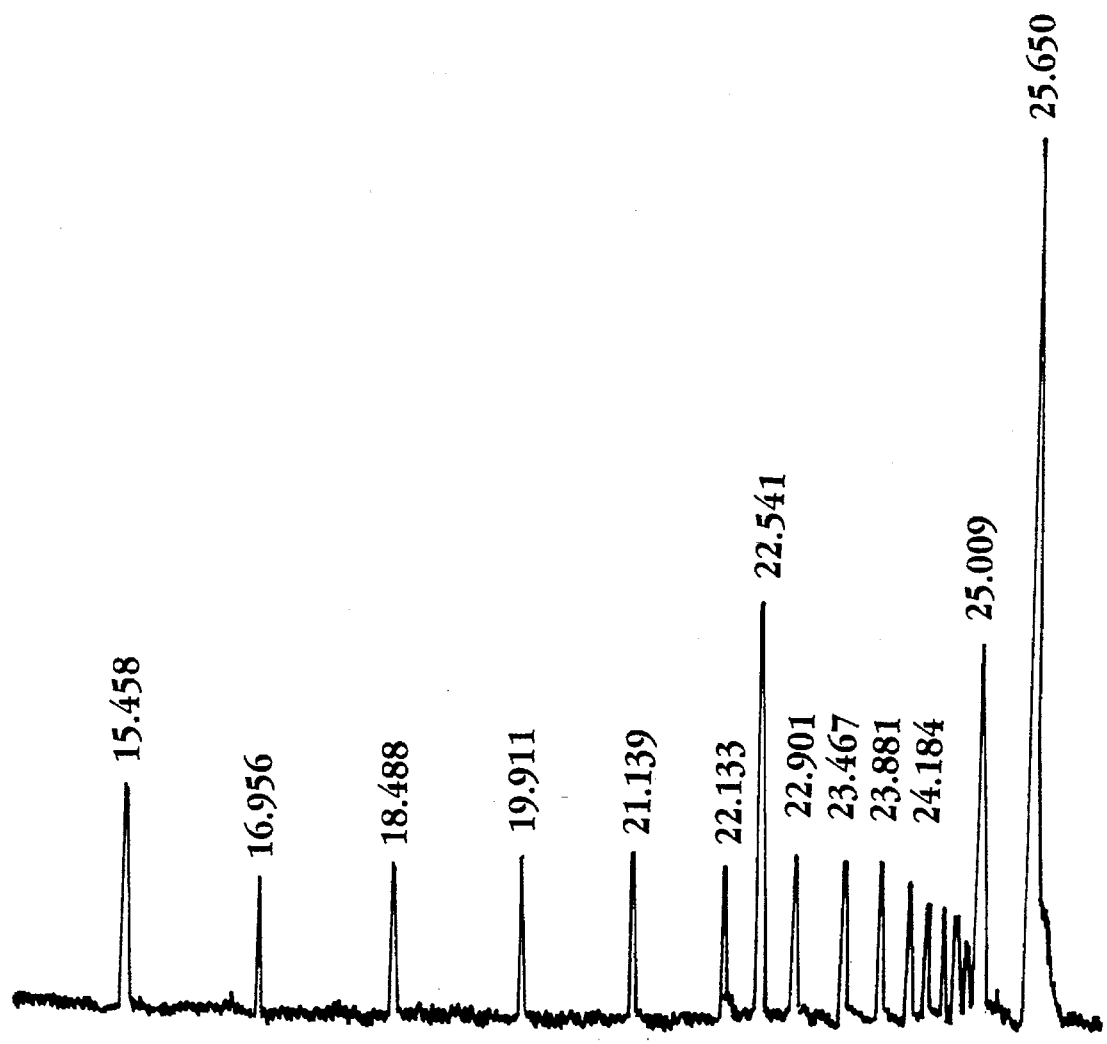
FIG. 4 is an electropherogram of a 100 basepair DNA ladder separated in a 3% poly(dimethyacrylamide) solution (RM18) in a TBE buffer.

A 3% (w:v) RM18 PDMA polymer in a 90 mM TBE buffer pH 8.3 was used to separate the components of the double stranded DNA ladder of Example 4. An Applied Biosystems model 270 HT was fitted with a 75 µm inside diameter uncoated fused silica capillary having 60 cm total length and 40 cm from the sample injection port to detector. Electrophoresis was carried out under 10 kV and 8 µA at 30° C. The sample was electrokinetically injected under 5 kV and 8 µA for 5 seconds. An electropherogram of the analyte (showing UV absorption at 260 nm) is illustrated in FIG. 4.

EXAMPLE 7

Electrophoresis of 100 basepair DNA ladder using 3% Polyacrylamide with and without 0.05% PDMA (RM18) in a 0.1 Glycylglycine Buffer A 3% (w:v) linear polyacrylamide solution in a 0.1M glycylglycine buffer pH 8.0 was used to separate the components of the double stranded DNA ladder of Example 4. An Applied Biosystems model 270 HT was fitted with a 75 µm inside diameter uncoated fused silica capillary having 60 cm total length and 40 cm from the sample injection port to detector. Electrophoresis was earfled out under 10 kV and 17 µA at 30° C. The sample was electrokinetically injected under 5 kV and 8 µA for 5 seconds. After 30 minutes no peaks were detected indicating that there was no separation of ladder components.

Figure 5:
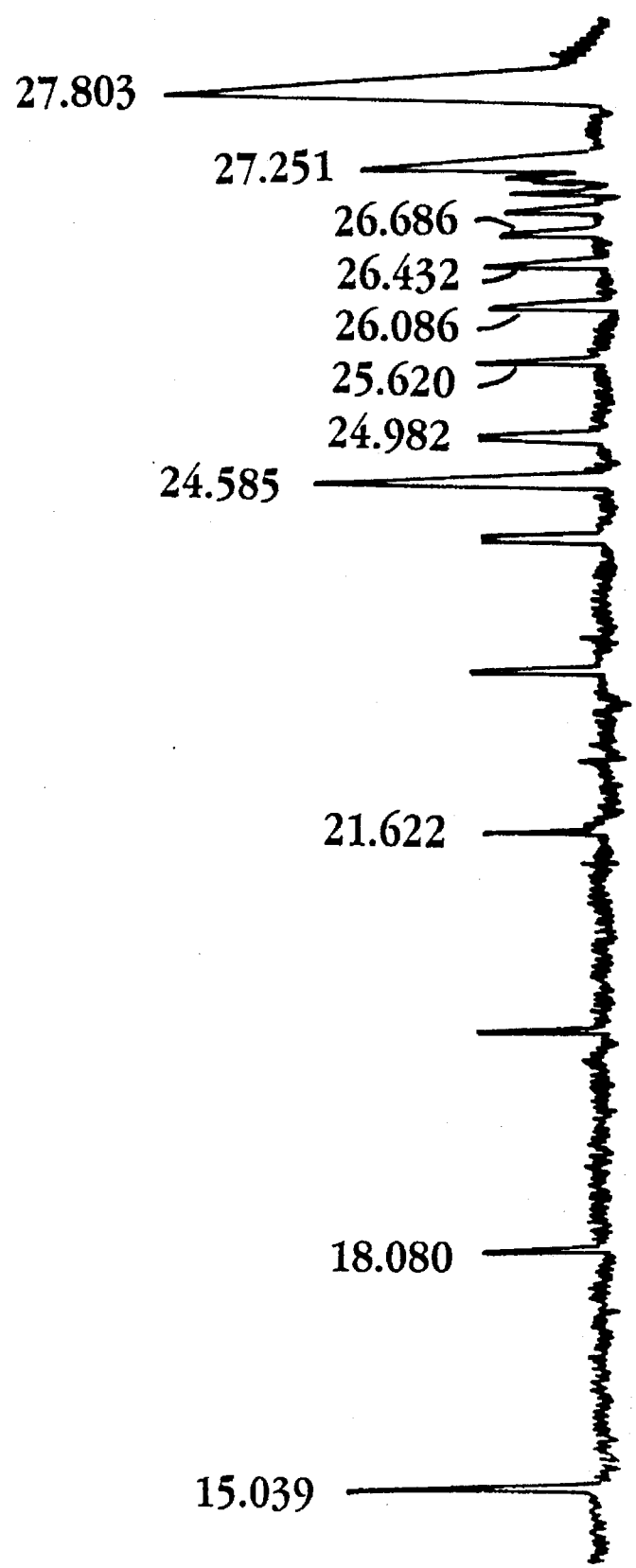
FIG. 5 is an electropherogram of a 100 basepair DNA ladder separated in a binary polymer solution comprising 3% polyacrylamide and 0.05% poly(dimethylacrylamide) (RM18) in a glycylglycine buffer.
Figure 6A:
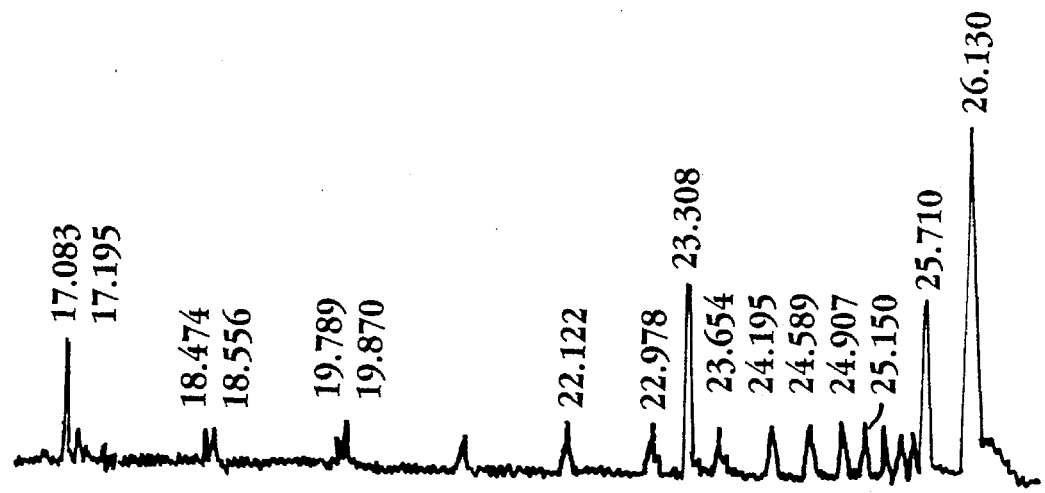
FIGS. 6A to 6F are electropherograms of a 100 basepair DNA ladder separated in various binary polymer solutions.
Figure 6B:
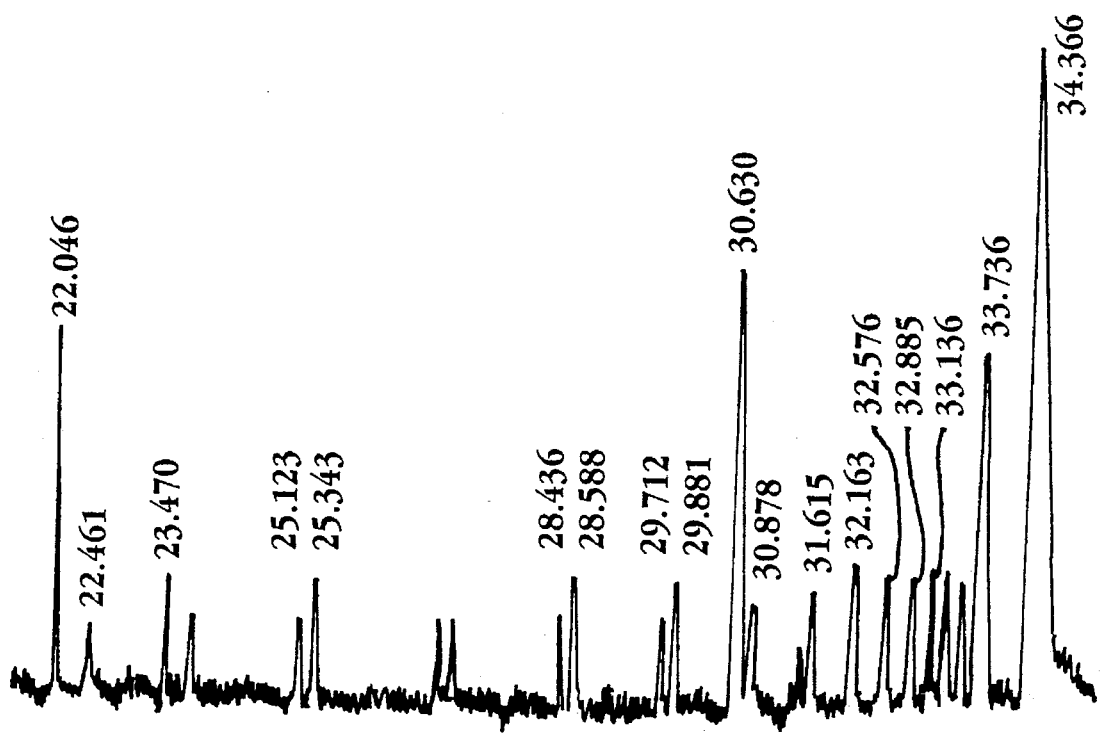
Figure 6C:
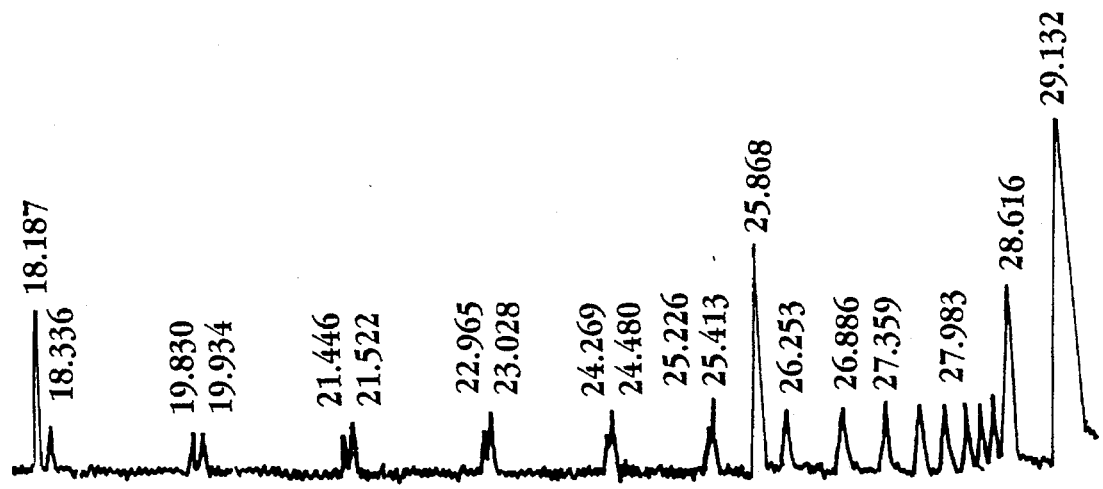
Figure 6D:
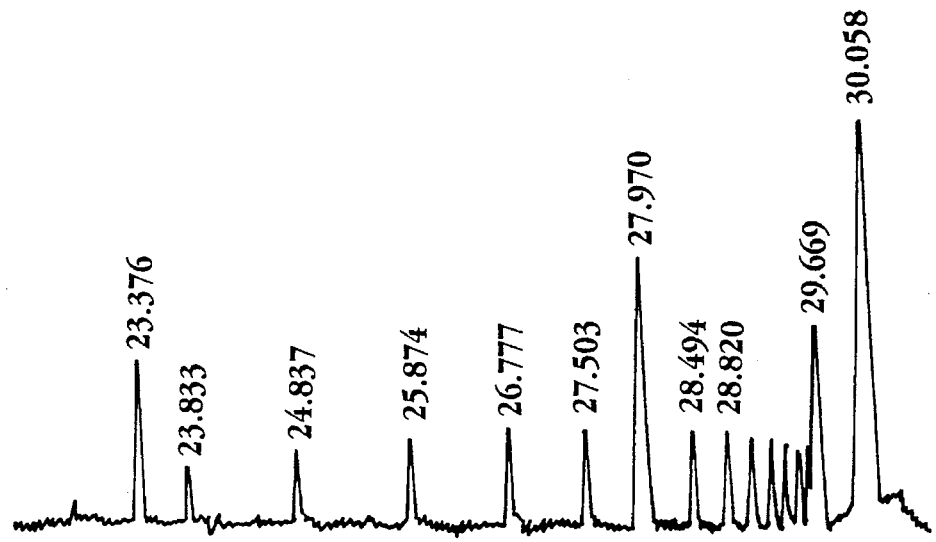
Figure 6E:
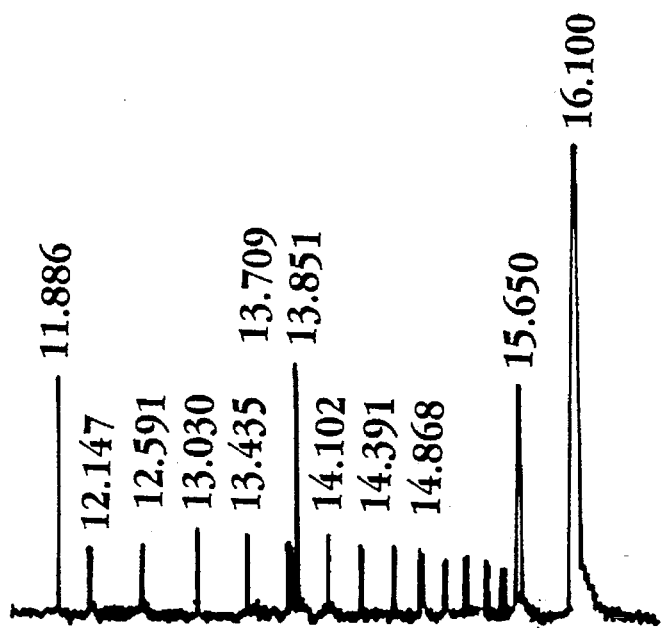
Figure 6F:
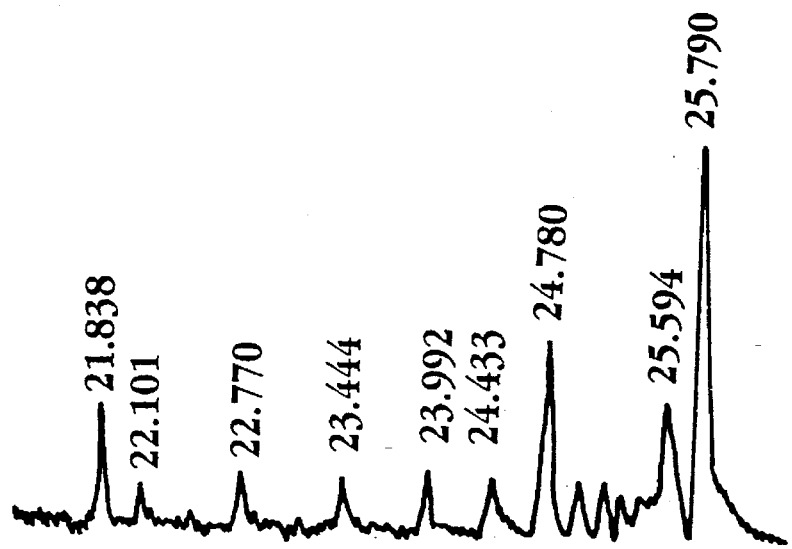
Figure 7A:
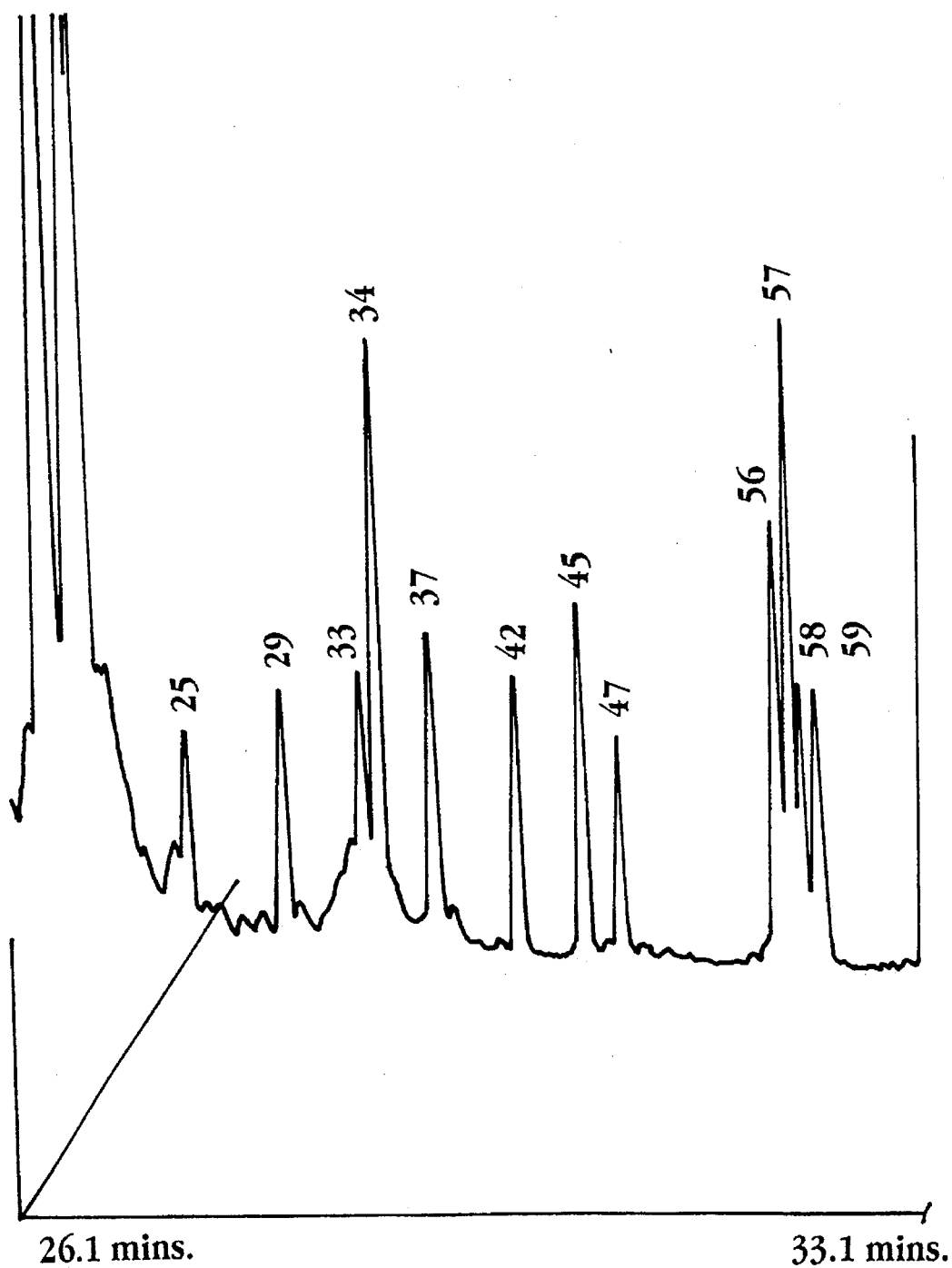
FIGS. 7A to 7J is an electropherogram of a commercially available DNA sequencing fragment standard separated in a separation medium containing a 6.5% solution of poly(dimethylacrylamide).
Figure 7B:
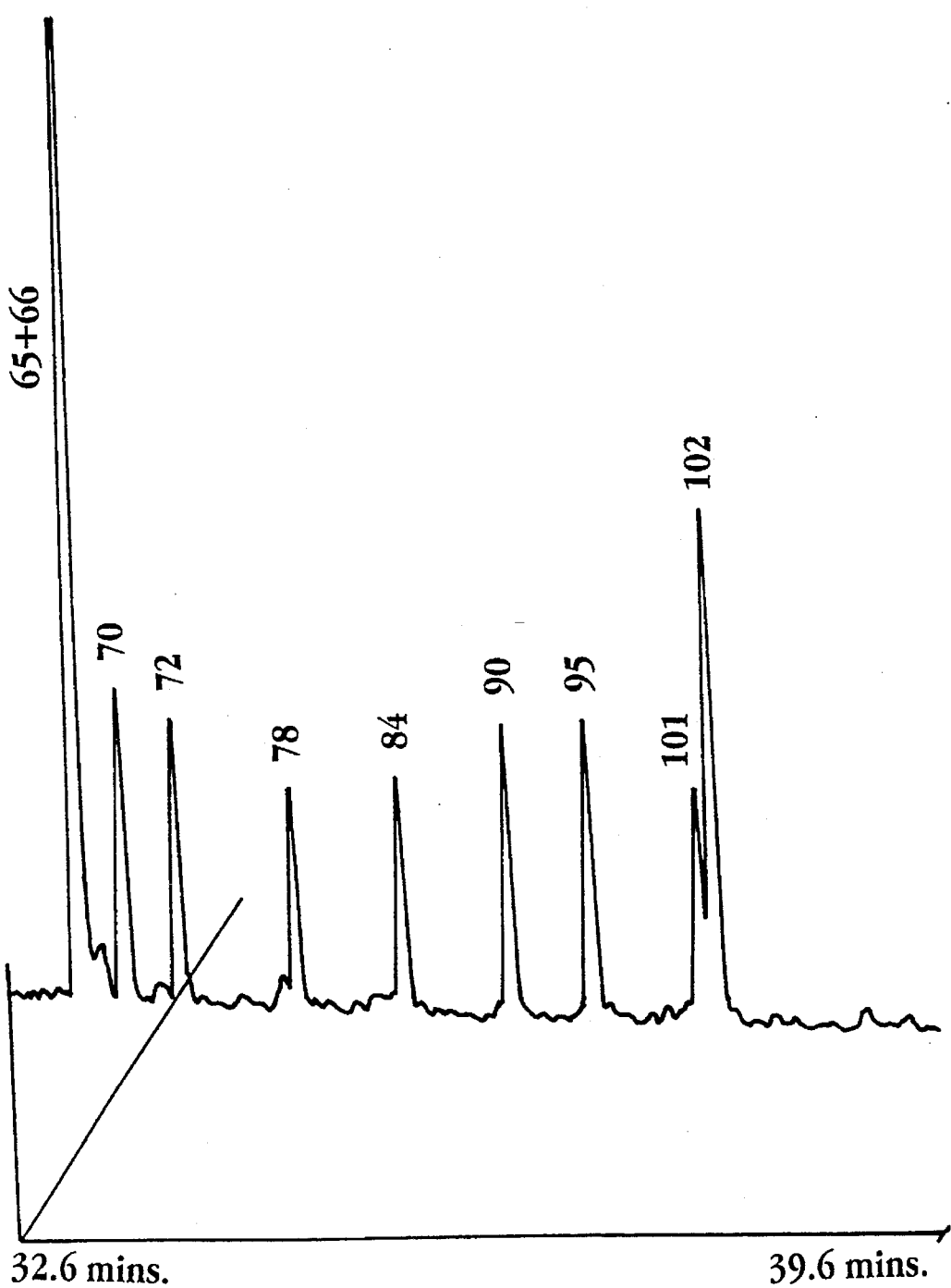
Figure 7C:
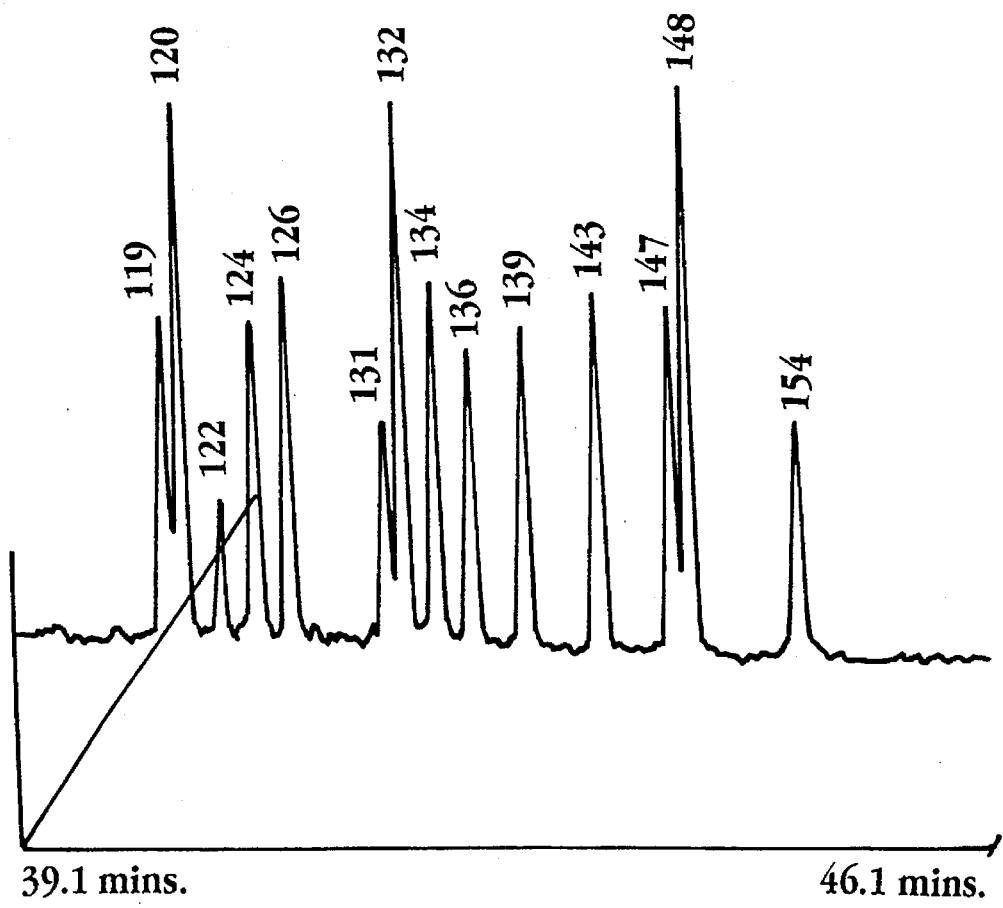
Figure 7D:
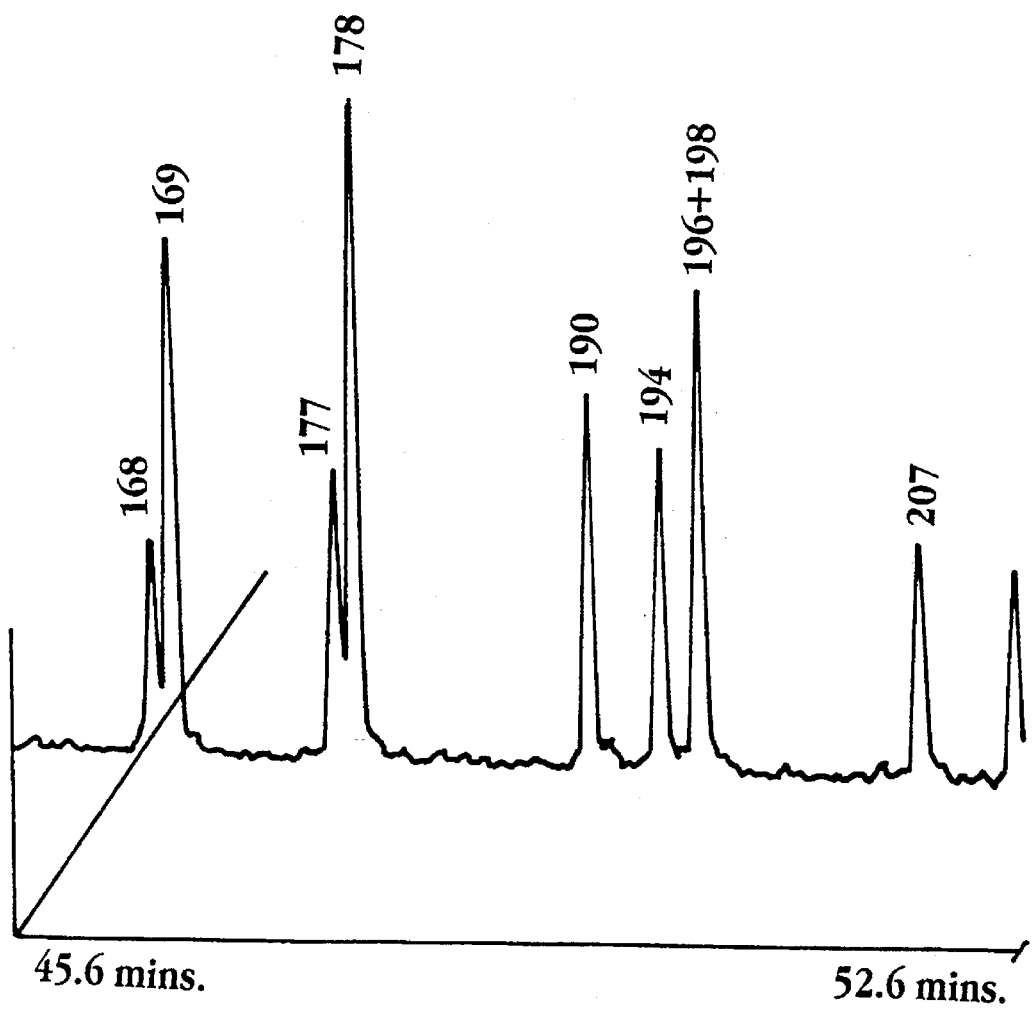
Figure 7E:
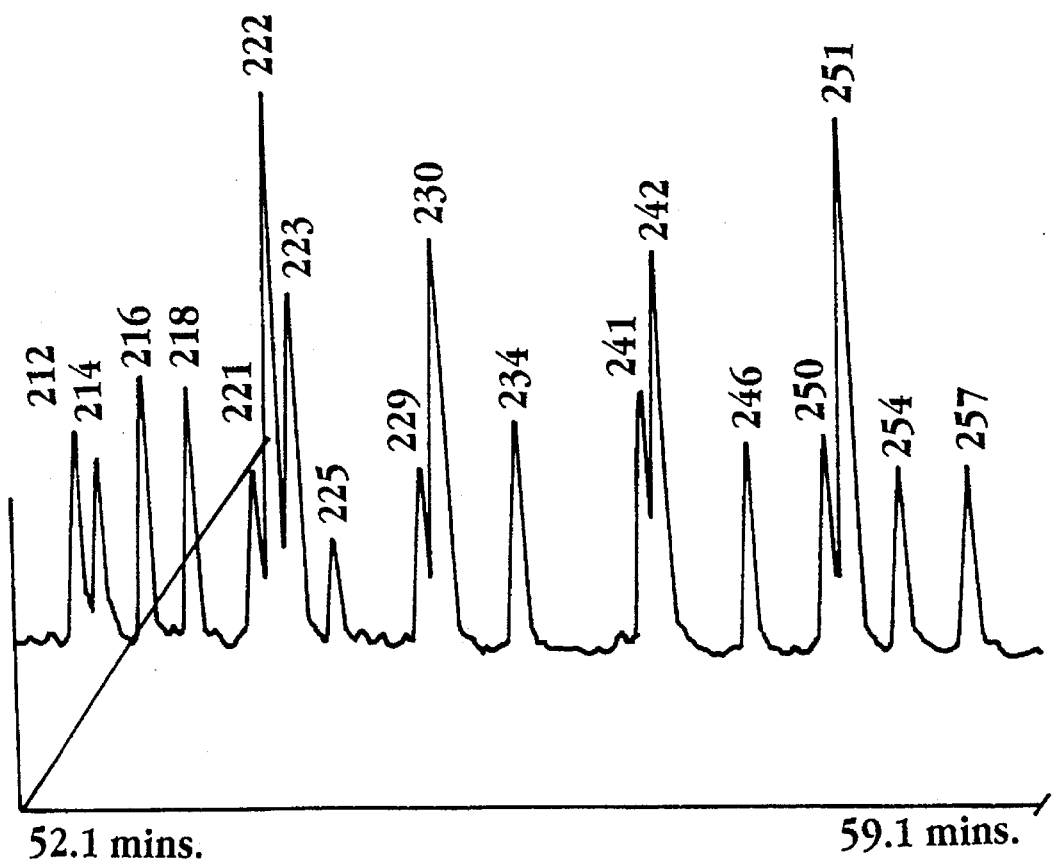
Figure 7F:
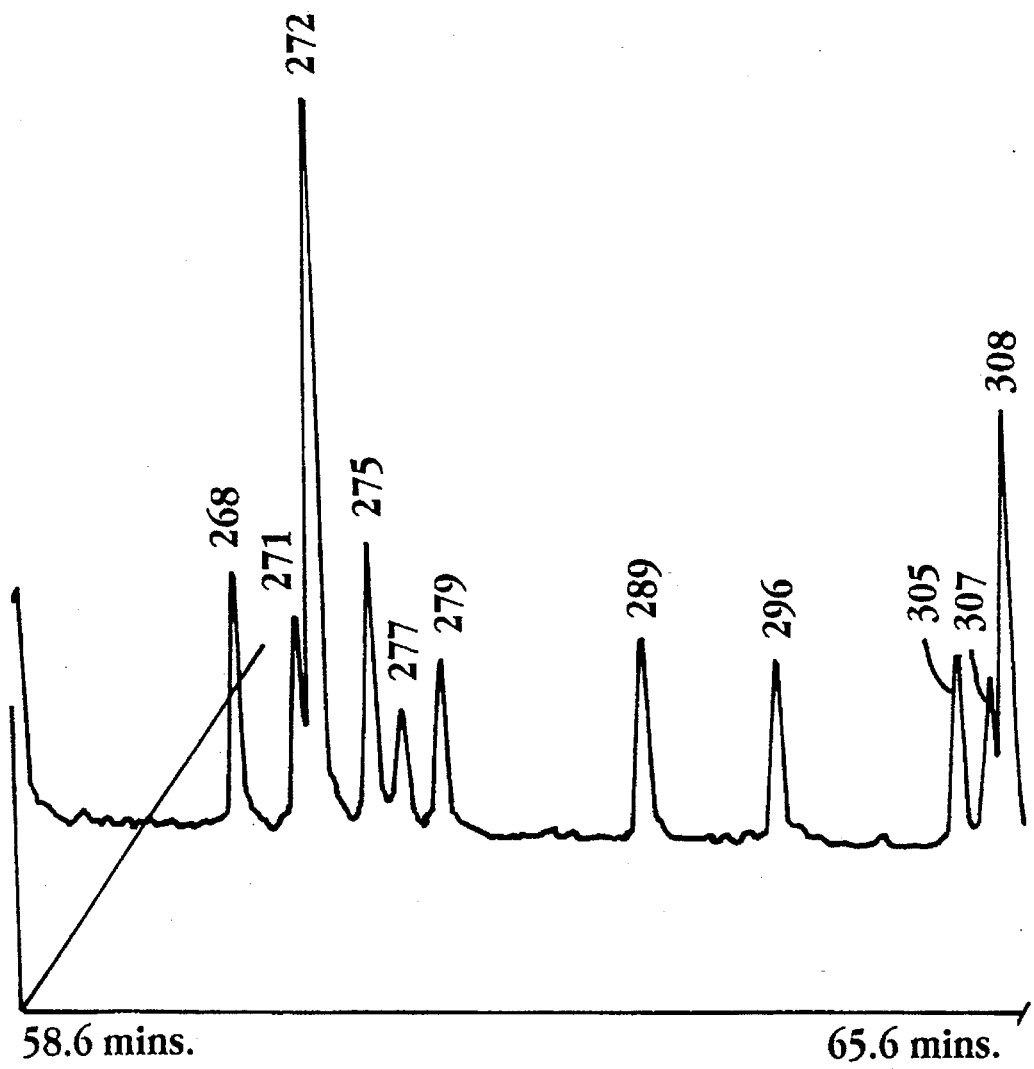
Figure 7G:
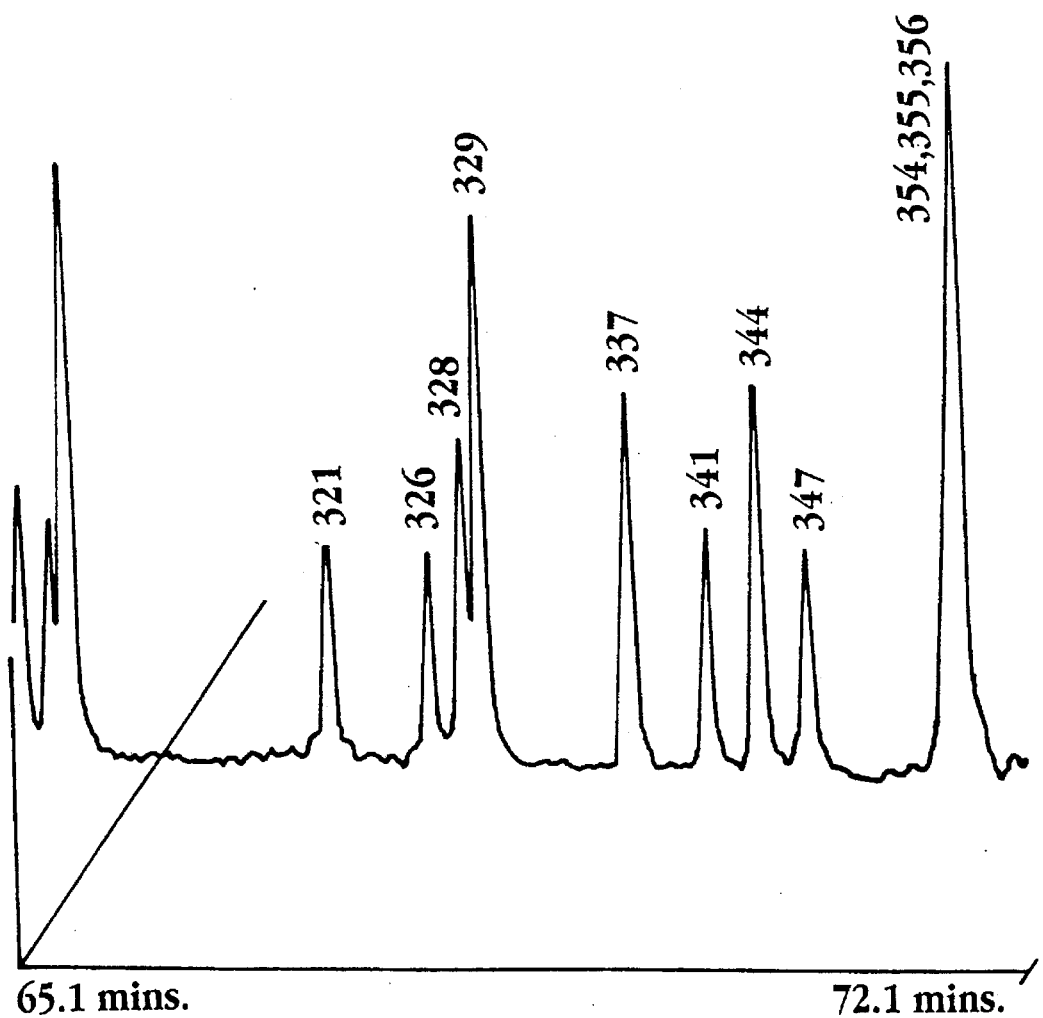
Figure 7H:
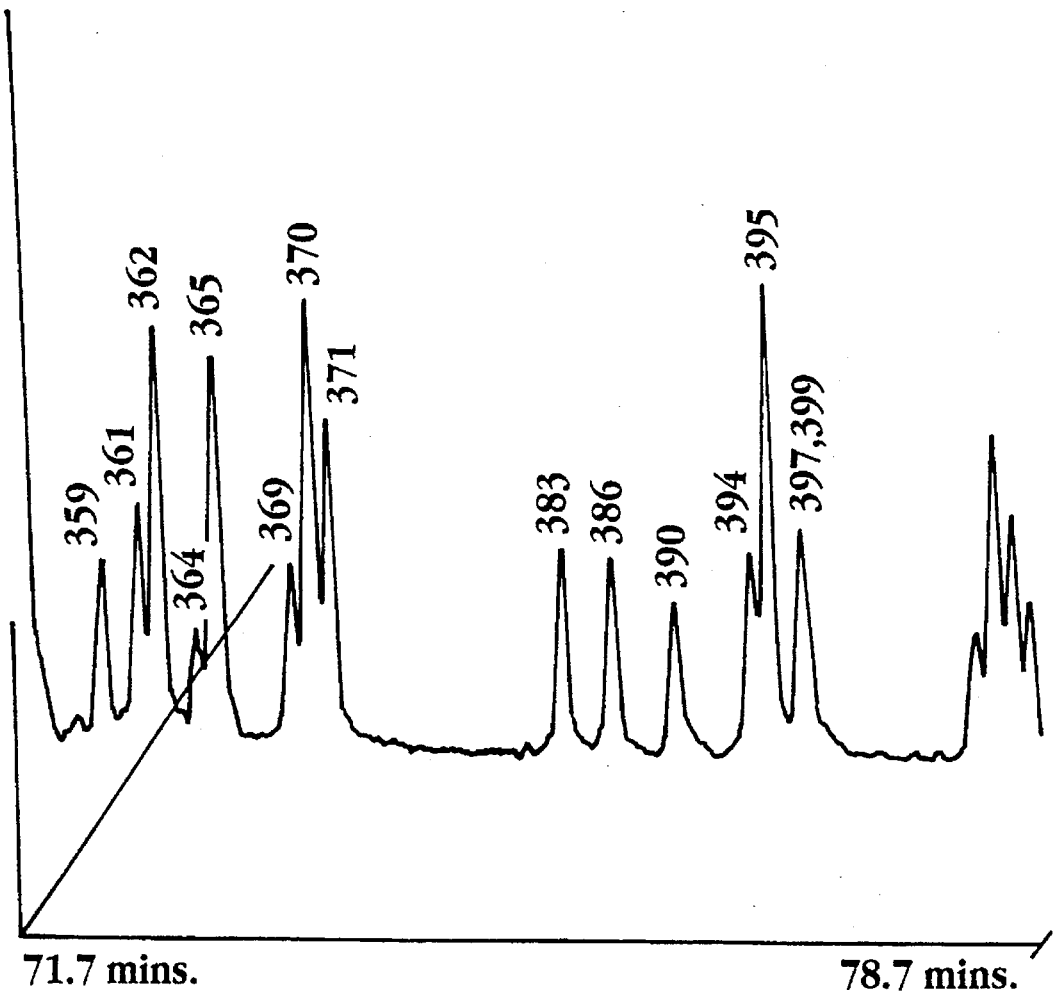
Figure 7I:
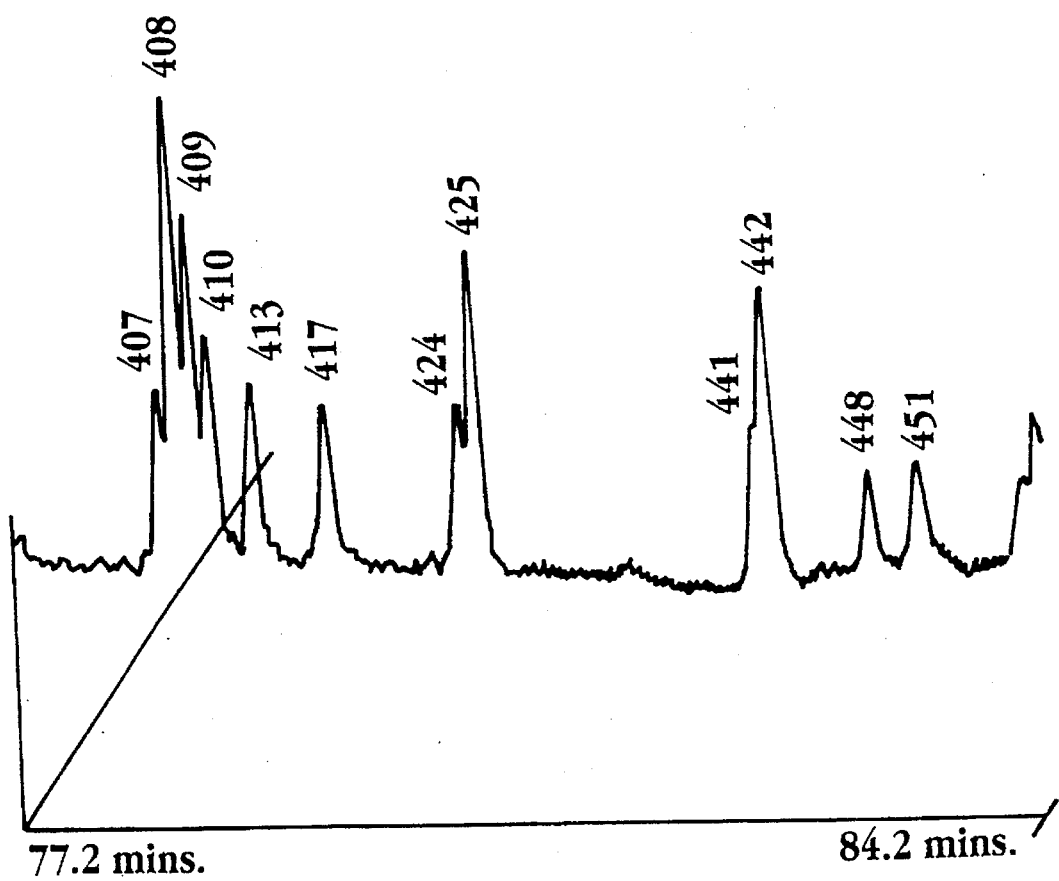
Figure 7J:
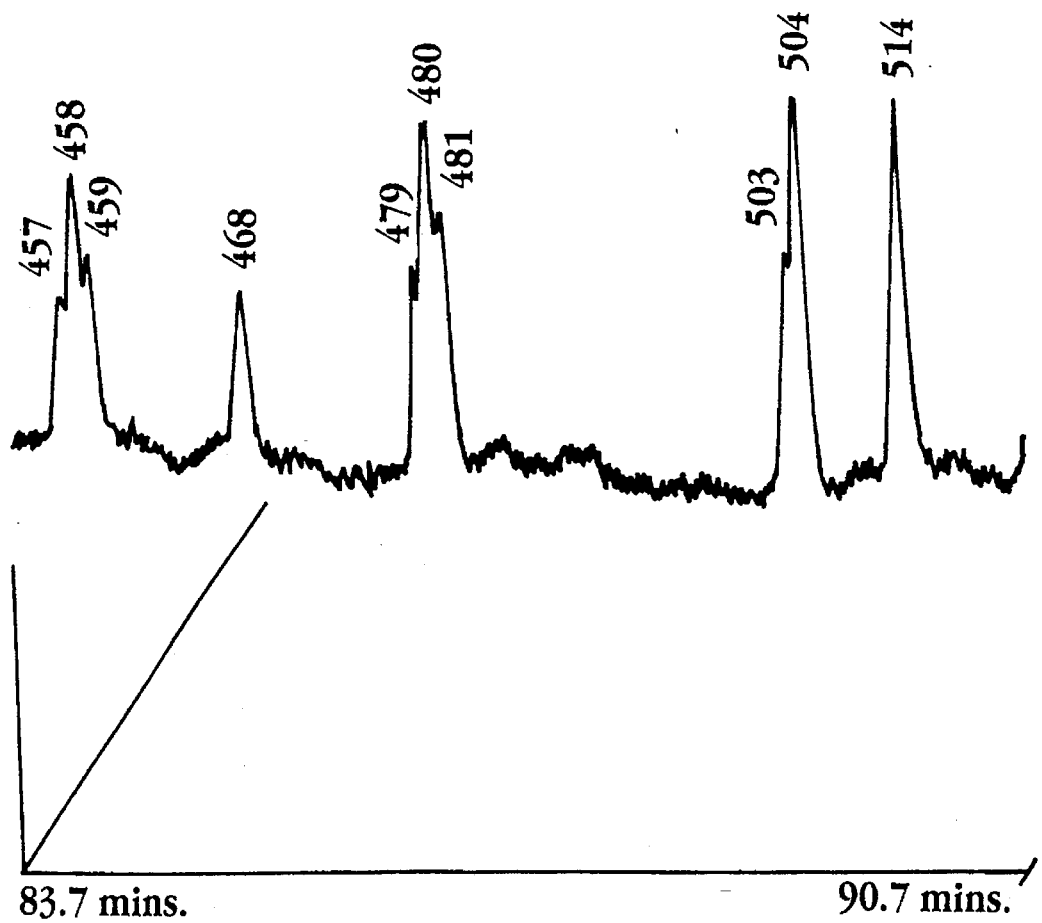
Figure 8A:
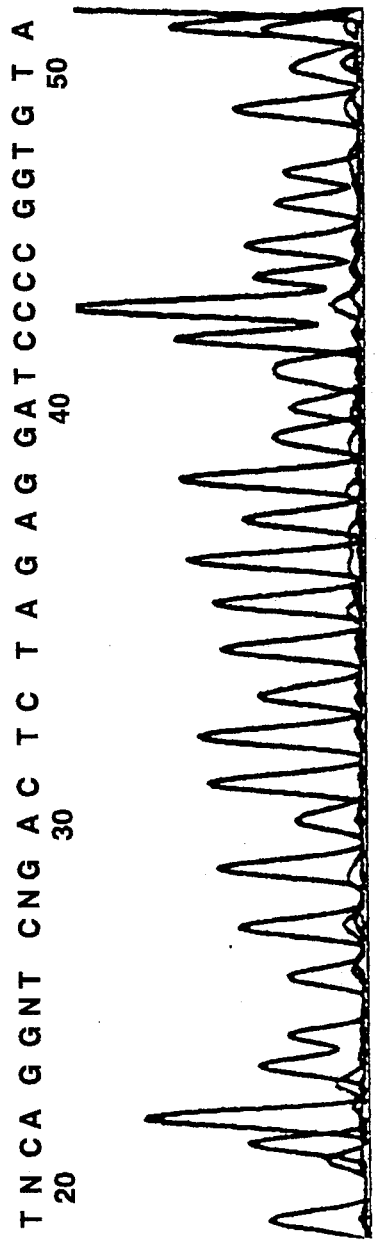
FIGS. 8A to 8F are an electropherogram showing the separation and sequencing of a 4-color sequencing standard in a separation medium containing a 6.5% solution of poly(dimethylacrylamide). The numbers above the peaks refer to the base number in the sequence, and the letters above each peak refer to the identity of the base.
Figure 8B:
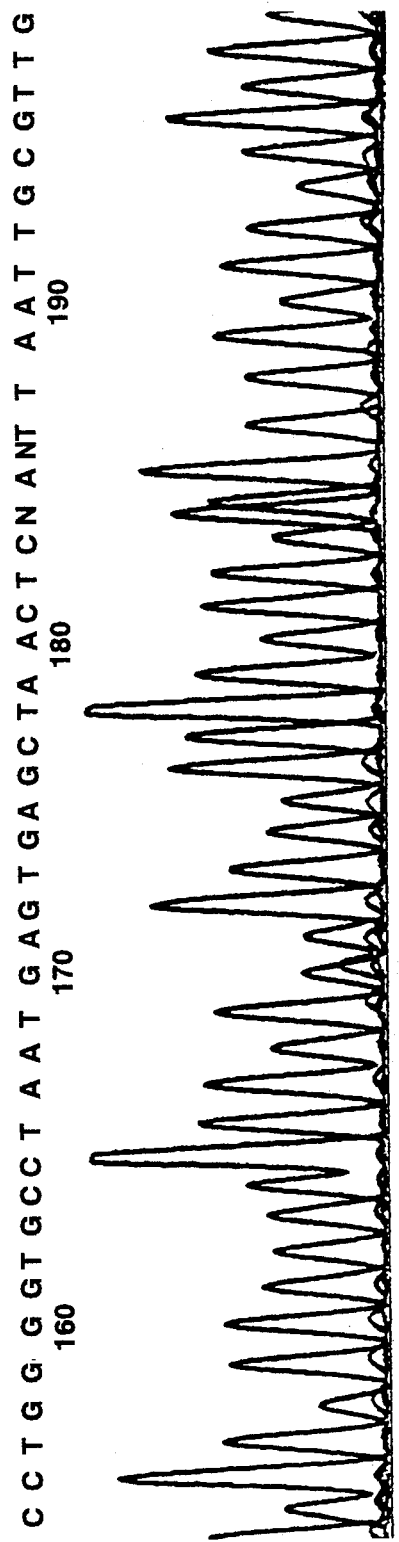
Figure 8C:
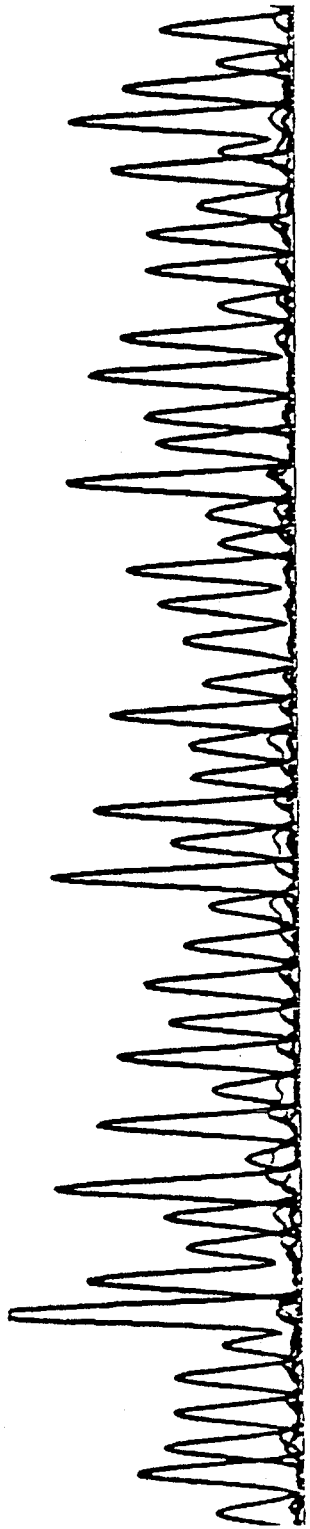
Figure 8D:
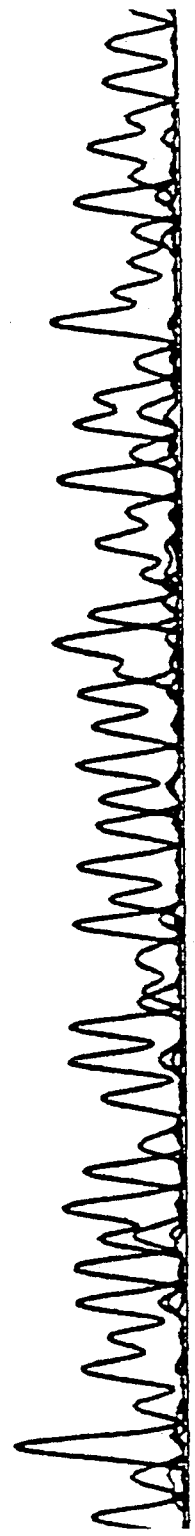
Figure 8E:
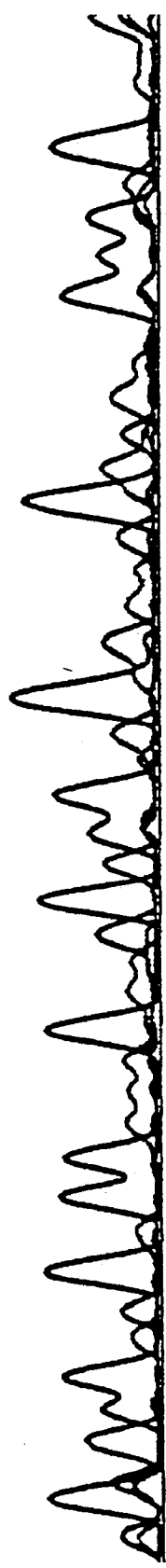
Figure 8F:
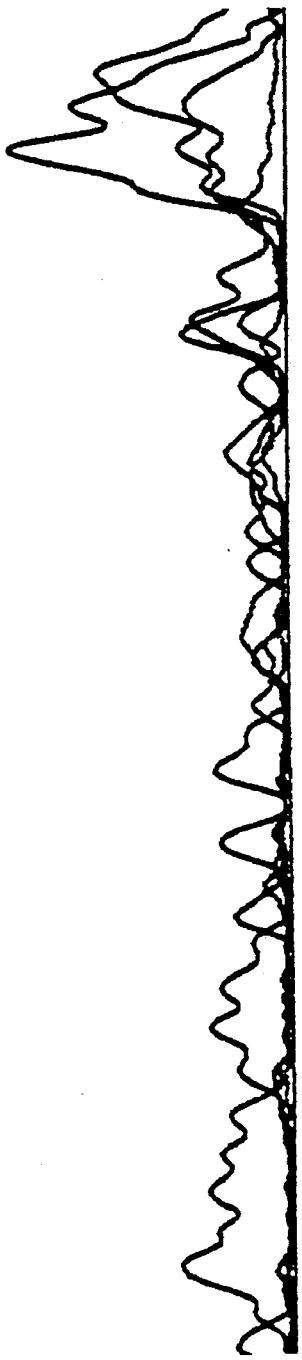
Figure 9A:
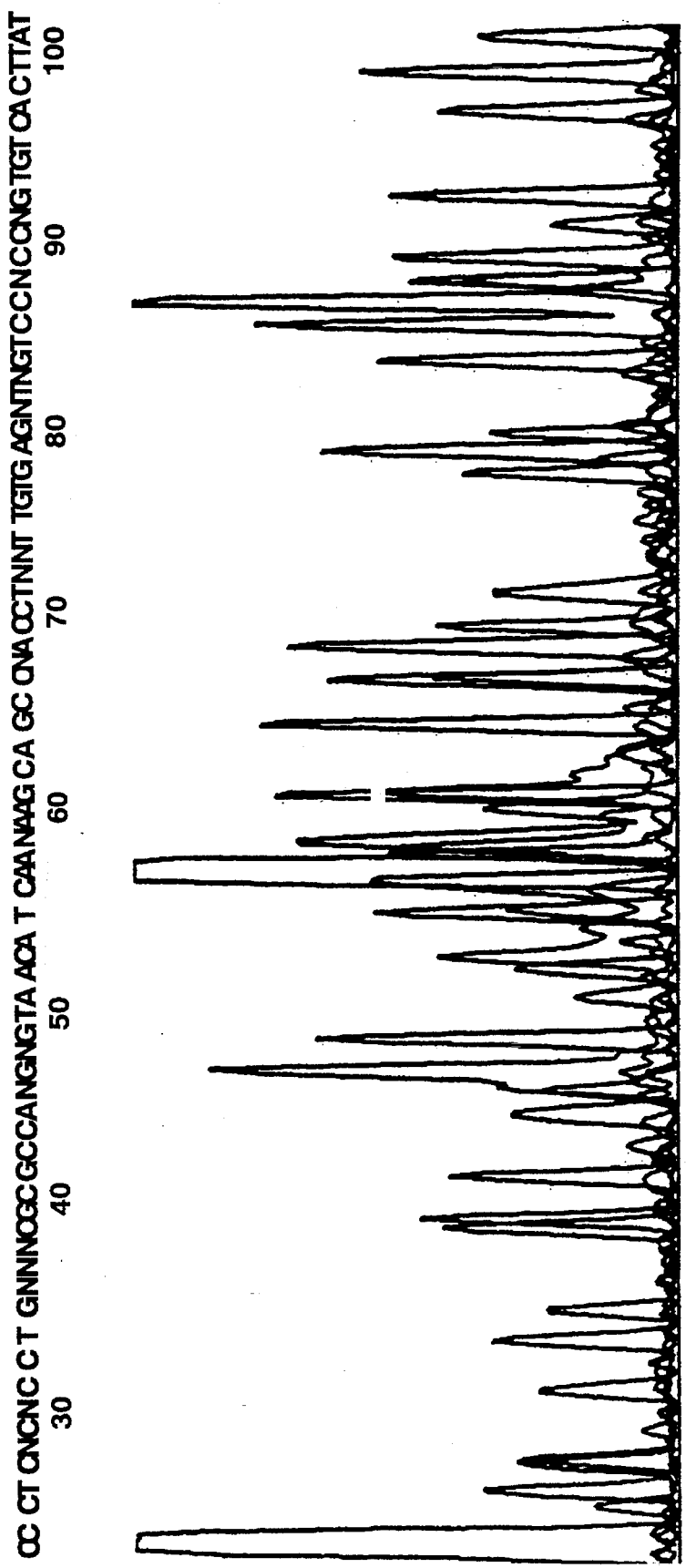
FIGS. 9A to 9F are an electropherogram showing the separation and sequencing of a 4-color sequencing standard in a separation medium containing a 10% solution of polyvinylpyrrolidone. The numbers above the peaks refer to the base number in the sequence, and the letters above each peak refer to the identity of the base.
Figure 9B:
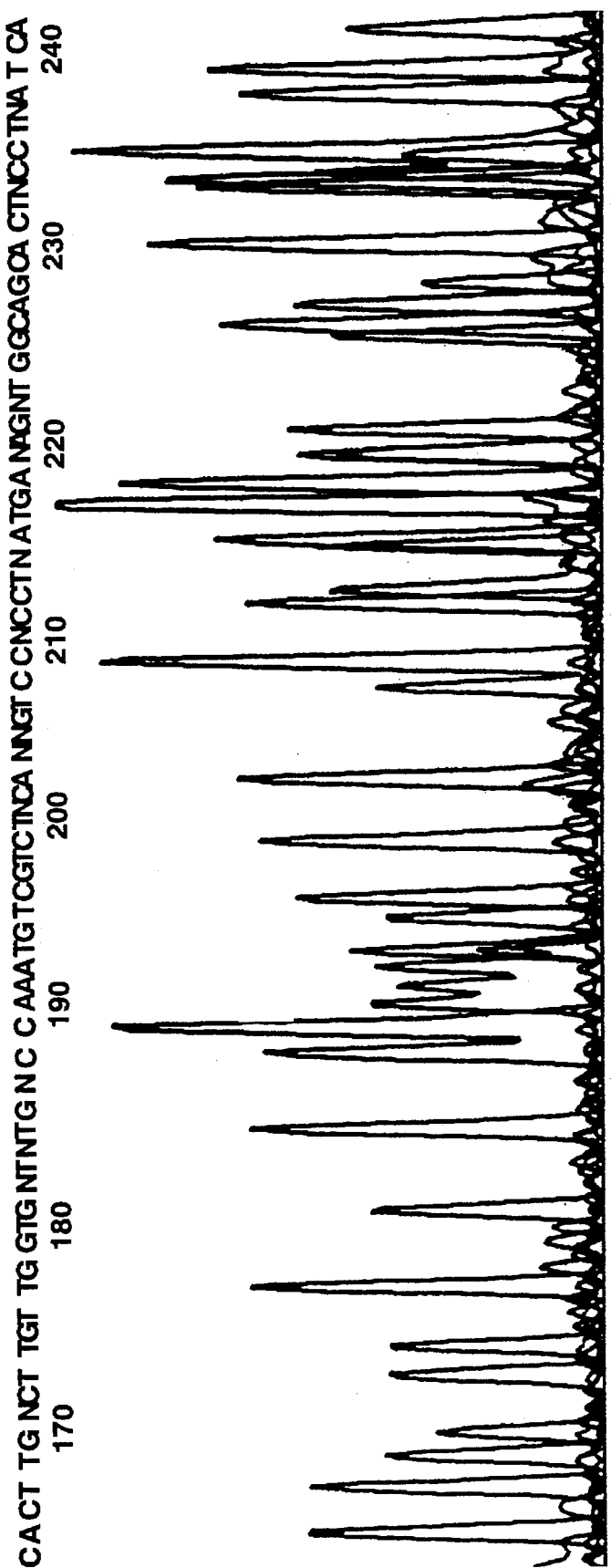
Figure 9C:
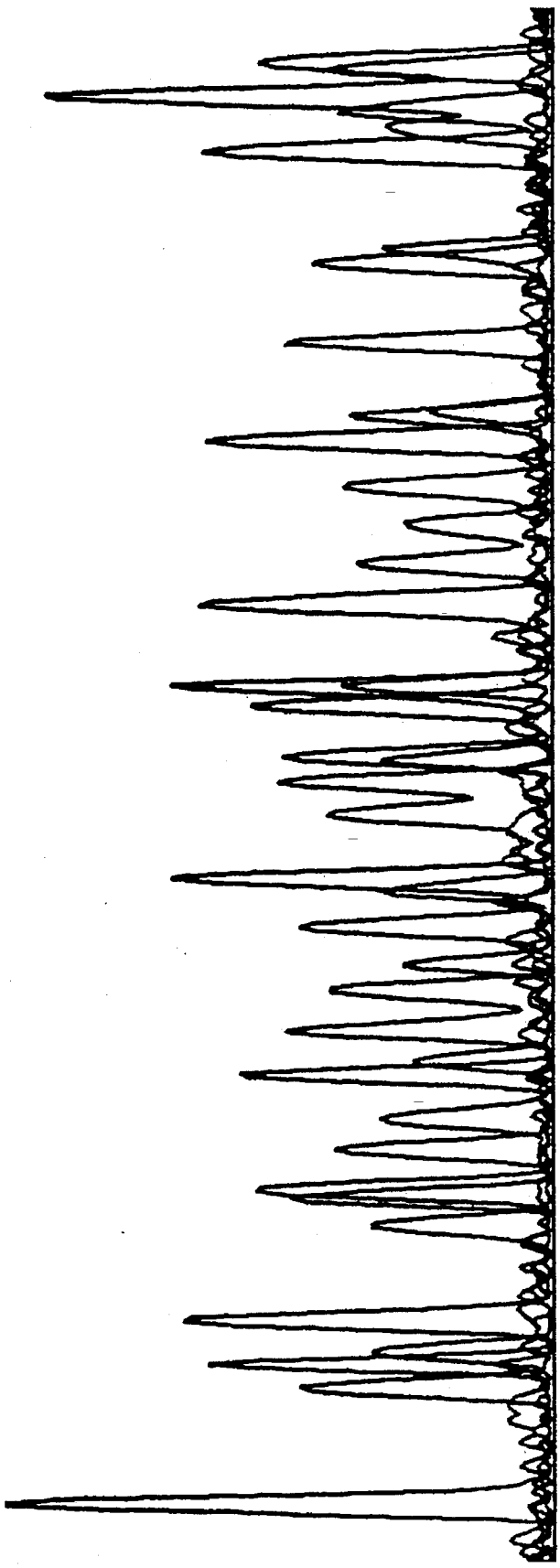
Figure 9D:
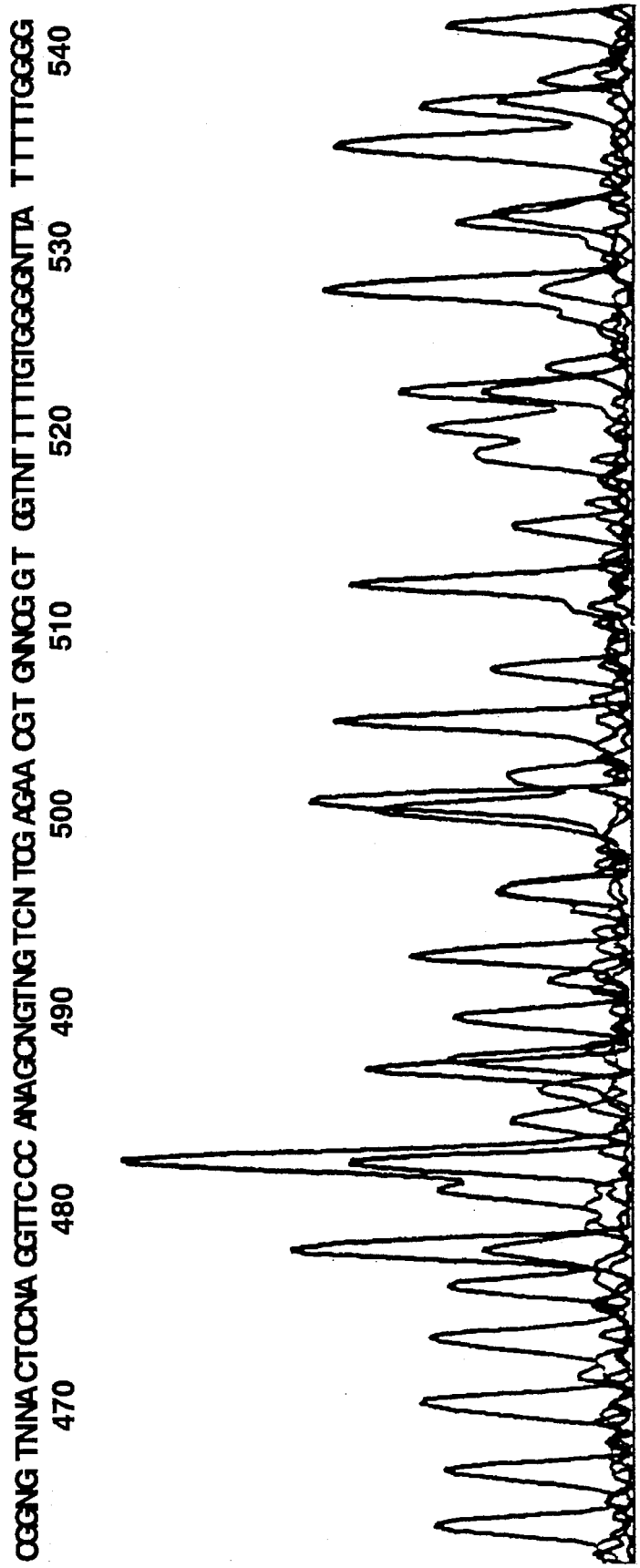
Figure 9E:
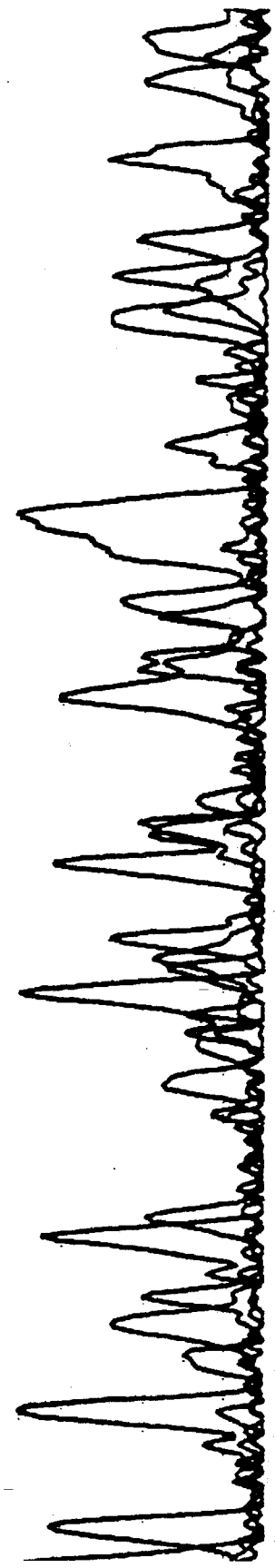
Figure 9F:

A second separation was conducted under identical conditions, except that the polymer solution used was a mixture of 3% linear polyacrylamide and 0.05% PDMA (RM18). An electropherogram of the analyte (showing UV absorption at 260 nm) is illustrated in FIG. 5.

EXAMPLE 8

Electrophoresis of 100 basepair DNA ladder using Polymer Solutions of Polyethylene oxide and Poly-N-vinylpyrrolidone in 0.1M Glycylglycine Buffers A 3% (w:v) solution of poly-N-vinylpyrrolidone (PVP) (average MW 360 kD) and a 5% (w:v) solution of polyethylene oxide (PEO) (average MW 35 kD) were prepared in 0.1M glycylglycine buffers pH 8.0. The DNA ladder of Example 4 was electrophoretically separated in six separate experiments using the same apparatus and under the same conditions as used in Examples 4–7 with the exception that different polymer solutions were employed. The polymer solutions are listed in the table below with reference to the Figures illustrating the degree of separation accomplished. The poly(dimethylacrylamide) used was RM18.

| Polymer Solution | Separation | Figure |
| --- | --- | --- |
| 3% PVP | Yes | 6A |
| 6% PVP | Yes | 6B |
| 3% PVP + 0.5% PDMA | Yes | 6C |
| 5% PEO | No | No figure |
| 5% PEO + 0.5% PDMA | Yes | 6D |
| 0.5% PDMA | Yes | 6E |
| 5% PEO + 0.05% PDMA | Yes | 6F |

EXAMPLE 9

Separation of DNA Sequencing Fragments in Poly(dimethylacrylamide) by Capillary Electrophoresis Fluorescently labelled DNA sequencing fragments were obtained from Applied Biosystems, Inc. (Foster City, Calif.) (The fragments used were the "C"-terminated fragments used to make up the 4-color sequencing standard supplied by Applied Biosystems as Part No. 400993, Taq DNA Sequencing Standard). 8 µl of the mixture containing fragments terminating with dideoxycytidine and labelled with fluorescein (FAM-C fragments) was added to a 500 µl centrifuge tube and dried in a speed vac using moderate heating. After adding 0.5 ml 50 mM EDTA solution and 6 ml recrystalized formamide to the dried FAM-C fragments, the mixture was heated at 95° C. for 2 min then placed on ice.

A separation medium for electrophoresis was prepared as follows: A stock buffer was prepared by mixing 20 ml methanol 110 ml water and 2.8 g Tris followed by titration with 85% phosphoric acid to pH 8.0. The separation medium was prepared by mixing 3.6 ml stock buffer, 3.6 ml water, 4.8 g urea, and 0.65 g poly(dimethylacrylamide) prepared as described above (RM21) to give a total volume of approximately 10 ml. The resulting mixture was stirred for 3 hours then filtered through a 0.45 µm syringe filter.

An uncoated 50 µm inside diameter Polymicro Technologies fused silica capillary (Cat. No. 2000017) of total length 54 cm was prepared so that there was 40 cm between the injection inlet and the detection zone. Prior to the first use, the capillary was flushed with 20 column volumes of 1.0M NaOH, 20 column volumes of water, then filled with separation medium. In subsequent runs with the same capillary, prior to use, the capillary was flushed with 20 column volumes of water, 20 column volumes tetrahydrofuran (THF), 20 column volumes 1M NaOH, 20 column volumes of water, then filled with separation medium.

The FAM-C fragment sample was electrokinetically loaded into the capillary under 1.8 kV at 0.69 µA for 25 sec, taking care to keep the electrode and the end of capillary as far apart as possible. The fragments were separated under 220 V/cm at 4.41 µA. Both sample injection and electrophoresis took place at 22° C. Fragment bands were illuminated at the detection window with an excitation beam from an argon ion laser (model 221-40MLA, Cyonics, San Jose, Calif.) operating at 1.5 mW. The excitation beam was passed through a 0.5 optical density neutral density filter (#FNG 085, Melles Groit, Irvine, Calif.) and into a set of focusing optics composed of a 64 mm focal length 7 mm diameter positive lens and an 85 mm focal length 5 mm diameter negative lens, resulting in a beam diameter of approximately 100 µm focused on the capillary detection window. Fluorescence emission was collected at right angles by a 12 mm focal length 14 diameter aspheric collector lens and passed through a 530 mn RDF bandpass filter (Omega Optical, Brattleboro, Vt.) and to a Fabry set composed of a 48 mm focal length 19 mm diameter aspheric Fabry lens followed by a 17 mm 10 mm diameter spherical Fabry lens. The light was then imaged on a photomultiplier tube (#R98-21, Hamamatsu, San Jose, Calif.) for detection. The electropherogram of the separated fragments is shown in FIGS. 7A–7J. The numbers adjacent to the peaks indicate the fragment size.

EXAMPLE 10

4-Color DNA SequenCing Analysis in Poly(dimethylacrylamide) by Capillary Electrophoresis Fluorescently labeled DNA sequencing fragments were obtained from Applied Biosystems, Inc. (Foster City, Calif.) (Part No. 400993, Taq DNA Sequencing Standard). To the dry Sequencing Standard were added 30 µl of a sample loading reagent made up of 0.15% hydroxyethylcellulose (QP 100MH Union Carbide) dissolved in a water-pyrrolidone (75:25 (vol:vol)) solvent. The sample was then divided into two 15 µl aliquots, heated at 95° C. for 2 min, and placed on ice.

The separation medium was prepared by dissolving 0.65 g poly(dimethylacrylamide) prepared as described above (RM21) and 4.8 g urea in a solution of 1.0 ml 1.0M TAPS (N-tris[Hydroxymethyl]methyl-3-aminopropanesulfonic acid), pH 8.0, and 6.2 ml water. The polymer solution was stirred overnight then filtered through a 0.45 gm syringe filter. The viscosity of the final polymer solution was approximately 75 cp at 25° C. as measured in a Brookfield viscometer Model DV-II using spindle#00 at a speed of approximately 50 rpm (Brookfield Engineering Laboratories, Sloughton, Mass.).

An uncoated 50 µm inside diameter fused silica capillary (Polymicro Technologies, Tucson, Ariz. Cat. No. 2000017) of total length 51 cm was prepared so that there was 40 cm between the injection inlet and the detection zone. Prior to the first use, the capillary was flushed with greater than 20 column volumes of water, followed by greater than 20 column volumes of 0.1M NaOH, followed by greater than 20 column volumes of water, then filled with separation medium.

The 4-color detection system used herein is similar to well known systems in the art of DNA analysis and is not a critical feature of the present invention, e.g., Karger et al., Nucleic Acids Research 19(18): 4955–62 (1991). The 4-color detection system utilizes an argon ion laser as a fluorescence-excitation light source that emits light at wavelengths of 488 and 514 nm. Typically the laser was operated at a total laser power of 9.9 mW. The laser light passes through a bandpass filter to remove the laser tube's cathode glow, the filter passing light having a wavelength of between approximately 485 nm and 515 nm. Next, a plano-convex lens diverges the light beam, the lens having a focal length of 100 mm and a diameter of 8 mm, e.g., Melles Griot part no. 01LPK041/078 (Melles Griot, Irvine, Calif.). The laser light then passes through a dichroic mirror which passes light having wavelengths of between approximately 485 nm and 515 nm, then passes through a microscope objective and into the detection region of the separation capillary. The emission light is reflected off of the dichroic mirror and directed toward a spectrograph. To reduce the amount of scattered laser light passing onto the spectrograph, the emission light passes through a long-pass filter having a cutoff of approximately 520 nm and is then focused onto an entrance slit of the spectrograph by a re-imaging lens having an 85 mm focal length, e.g., Melles Griot part no. 01LPK035. The spectrograph utilizes a 405 g/mm, 450 nm blaze grating with a dispersion of 17 nm/mm. After passing through the spectrograph, the light then falls onto a charged coupled device (CCD) detector. The output signal from the CCD is transmitted to electronic computer for subsequent data analysis and presentation. The software used for data analysis was the Sequencing Analysis version 2.1.0B1, which is similar to commercially utilized sequence analysis software (Applied Biosystems Model 373 DNA Sequencer), the basic algorithm of which is generally described elsewhere, e.g., Smith et al, Methods in Enzymology Vol. 155 pages 260–301, Academic Press (1991).

The sample was electrokinetically loaded into the capillary using a field of 60 V/cm for 25 sec. The fragments were separated under a field of 160 V/cm at 3.0 µA at a temperature of 42° C. The run was allowed to proceed for approximately two hours.

The resulting electropherogram is shown in FIG. 8.

EXAMPLE 11

4-Color DNA Sequencing Analysis in Polyvinylpyrrolidone by Capillary Electrophoresis The separation medium was prepared by dissolving 1.0 g polyvinylpyrrolidone (Povidone, United States Pharmacopia, BASF, Kollidon 90 F) and 4.8 g urea in a solution of 1.0 ml 1.0M TAPS (N-tris[Hydroxymethyl]methyl-3-aminopropanesulfonic acid), pH 8.0, and 6.2 ml water. The polymer solution was stirred overnight then filtered through a 0.45 µm syringe filter.

The DNA sequencing fragments, the fragment sample preparation, the electrophoresis capillary, the 4-color detection system, the sample injection protocol, and the electrophoresis run conditions were all essentially the same as those used in Example 10.

The resulting electropherogram is shown in FIG. 9.

No dye mobility correction was applied to the data shown in FIG. 9. Because the addition of fluorescent dyes to the DNA sequencing extension products alters the electrophoretic mobility of the asociated DNA fragments, and because different dyes cause different mobility shifts, a "mobility correction" is required to normalize the electrophoretic mobility of fragments containing different dyes. Because the data in FIG. 9 has not been corrected for these mobility shifts, the order of the peaks is offset somewhat. However, it is still possible to see that the requisite resolution of neighboring fragments has been achieved using the polyvinylpyrrolidone material.

We claim:

1. A method of suppressing electroendoosmotic flow and analyte-wall interactions in capillary electrophoresis, the method comprising providing a separation medium containing one or more uncharged water-soluble silica-adsorbing polymers having (i) water solubility in a temperature range between about 20° C. and about 50° C., (ii) a concentration in the separation medium in a range between about 0.001% and about 10% weight/volume, (iii) a molecular weight in the range between about $5\times10^3$ and about $1\times10^6$ daltons, (iv) an absence of charged groups in an aqueous medium having a pH in the range between about 6 and about 9; and the separation medium having a viscosity of less than about 1000 centipoise.

2. The method of claim 1 wherein said one or more uncharged water-soluble silica-adsorbing polymers are substantially non-hydroxylic.

3. The method of claim 2 wherein at least one of said one or more uncharged water-soluble silica-adsorbing polymer is a polylactam.

4. The method of claim 3 wherein at least one of said one or more uncharged water-soluble silica-adsorbing polymer is polyvinylpyrrolidone.

5. The method of claim 1 wherein at least one of said one or more uncharged water-soluble silica-adsorbing polymer is an N,N-disubstituted polyacrylamide or an N-substituted polyacrylamide, wherein said nitrogen substituents are selected from the group consisting of $C_1$ to $C_3$ alkyl; halo-substituted $C_1$ to $C_3$ alkyl; methoxy-substituted $C_1$ to $C_3$ akyl; and hydroxyl-substituted $C_1$ to $C_3$ akyl.

6. The method of claim 5 wherein said nitrogen substituents are selected from the group consisting of $C_1$ to $C_3$ alkyl; halo-substituted $C_1$ to $C_3$ alkyl; and methoxy-substituted $C_1$ to $C_3$ alkyl.

7. The method of claim 6 wherein said at least one of said one or more uncharged water-soluble silica-adsorbing polymer is poly(dimethylacrylamide).

8. The method of claim 7 wherein said electroendoosmotic flow is less than about $2\times10^{-5}$ cm$^2$/sec-volts.

9. The method of claim 7 wherein said one or more uncharged water-soluble silica-adsorbing polymers provides a substantially linear relationship between number of theoretical plates and size of polynucleotide in the size range of between about 100 and about 500 nucleotides.

10. A method of separating different-sized polynucleotides by electrophoresis in an uncoated silica capillary, the method comprising the steps of:

providing an uncoated silica capillary having a first end and a second end, the uncoated silica capillary containing a separation medium containing one or more uncharged water-soluble silica-adsorbing polymers having (i) water solubility in a temperature range between about 20° C. and about 50° C., (ii) a concentration in the separation medium in a range between about 0.001% and about 10% weight/volume, (iii) a molecular weight in the range between about $5 \times 10^3$ and about $1 \times 10^6$ daltons, (iv) an absence of charged groups in an aqueous medium having a pH in the range between about 6 and about 9; and the separation medium having a viscosity of less than about 1000 centipoise;

loading a sample of different-sized polynucleotide in the uncoated silica capillary; and applying an electrical field between the first and second ends of the uncoated silica capillary so that the different-sized polynucleotides in the sample migrate through the uncoated silica capillary.

* * * * *